(12) United States Patent
Torres et al.

(10) Patent No.: US 10,086,175 B2
(45) Date of Patent: Oct. 2, 2018

(54) BALLOON CATHETER

(71) Applicant: Abbott Cardiovascular Systems Inc., Santa Clara, CA (US)

(72) Inventors: Hector Torres, Temecula, CA (US); Bruce Wilson, Temecula, CA (US); Thomas Haslinger, Sun City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 206 days.

(21) Appl. No.: 14/843,249

(22) Filed: Sep. 2, 2015

(65) Prior Publication Data

US 2016/0067458 A1    Mar. 10, 2016

Related U.S. Application Data

(60) Provisional application No. 62/046,157, filed on Sep. 4, 2014.

(51) Int. Cl.
| | |
|---|---|
| *A61M 25/10* | (2013.01) |
| *A61L 29/06* | (2006.01) |
| *A61M 25/01* | (2006.01) |

(52) U.S. Cl.
CPC .............. *A61M 25/10* (2013.01); *A61L 29/06* (2013.01); *A61M 25/1034* (2013.01); *A61M 2025/0183* (2013.01)

(58) Field of Classification Search
CPC .......... A61M 25/0045; A61M 25/0067; A61M 25/0068; A61M 25/0069;
(Continued)

(56) References Cited

U.S. PATENT DOCUMENTS

| | | |
|---|---|---|
| 4,522,867 A | 6/1985 | Hill, Jr. et al. |
| 4,782,834 A | 11/1988 | Maguire et al. |

(Continued)

FOREIGN PATENT DOCUMENTS

| | | |
|---|---|---|
| EP | 1 084 728 A1 | 3/2001 |
| EP | 1 306 062 A1 | 5/2003 |

(Continued)

OTHER PUBLICATIONS

U.S. Appl. No. 13/481,441 (U.S. Pat. No. 8,834,510), filed May 25, 2012 (Sep. 16, 2014).

(Continued)

*Primary Examiner* — Nathan R Price
*Assistant Examiner* — Courtney Fredrickson
(74) *Attorney, Agent, or Firm* — Baker Botts L.L.P.

(57) ABSTRACT

Catheter includes an outer shaft member having a proximal section and a distal outer member. The outer shaft has an inflation lumen defined therethrough. A balloon is in fluid communication with the inflation lumen and has a proximal balloon shaft, a proximal cone portion, a working length, a distal cone portion, and a distal balloon shaft. Catheter also includes a monolithic inner tubular member extending from the outer shaft proximal section through the distal outer member and through the balloon to form a tip. The distal balloon shaft has an inner diameter and comprises a distal seal portion coupled to the inner tubular member and a proximal portion free of attachment to the inner tubular member. The length of the proximal portion of the distal balloon shaft is at least about two times the inner diameter of the distal balloon shaft. Methods of making a catheter are also provided.

25 Claims, 15 Drawing Sheets

(58) Field of Classification Search
CPC ...... A61M 2025/0183; A61M 25/0053; A61M 25/0029
See application file for complete search history.

(56) References Cited

U.S. PATENT DOCUMENTS

| | | | |
|---|---|---|---|
| 4,976,690 A | | 12/1990 | Solar et al. |
| 5,156,594 A | | 10/1992 | Keith |
| 5,217,434 A | * | 6/1993 | Arney ............... A61M 25/0054 604/103.1 |
| 5,217,482 A | | 6/1993 | Keith |
| 5,279,562 A | | 1/1994 | Sirhan et al. |
| 5,370,616 A | | 12/1994 | Keith et al. |
| 5,370,655 A | | 12/1994 | Burns |
| 5,387,193 A | | 2/1995 | Miraki |
| 5,387,225 A | | 2/1995 | Euteneuer et al. |
| 5,395,334 A | | 3/1995 | Keith et al. |
| 5,423,754 A | | 6/1995 | Cornelius et al. |
| 5,458,615 A | | 10/1995 | Klemm et al. |
| 5,490,837 A | | 2/1996 | Blaeser et al. |
| 5,507,768 A | | 4/1996 | Lau et al. |
| 5,533,968 A | | 7/1996 | Muni et al. |
| 5,643,209 A | * | 7/1997 | Fugoso ............... A61M 25/008 604/103 |
| 5,649,909 A | | 7/1997 | Cornelius |
| 5,743,875 A | | 4/1998 | Sirhan et al. |
| 5,833,706 A | | 11/1998 | St. Germain et al. |
| 5,908,406 A | | 6/1999 | Ostapchenko et al. |
| 6,083,232 A | | 7/2000 | Cox |
| 6,102,890 A | | 8/2000 | Stivland et al. |
| 6,217,547 B1 | | 4/2001 | Lee |
| 6,277,093 B1 | | 8/2001 | Lee |
| 6,575,958 B1 | | 6/2003 | Happ et al. |
| 6,595,958 B1 | | 7/2003 | Mickley |
| 6,620,127 B2 | | 9/2003 | Lee et al. |
| 6,695,812 B2 | | 2/2004 | Estrada et al. |
| 6,702,802 B1 | * | 3/2004 | Hancock ............... A61F 2/958 604/104 |
| 6,746,423 B1 | | 6/2004 | Wantink |
| 6,923,822 B2 | | 8/2005 | Crawford et al. |
| 6,964,750 B2 | | 11/2005 | Fulford |
| 7,001,420 B2 | | 2/2006 | Speck et al. |
| 7,074,206 B2 | | 7/2006 | Lee et al. |
| 7,195,611 B1 | | 3/2007 | Simpson et al. |
| 7,303,798 B2 | | 12/2007 | Bavaro et al. |
| 7,322,959 B2 | | 1/2008 | Warnack et al. |
| 7,549,975 B2 | | 6/2009 | Lee et al. |
| 7,828,766 B2 | | 11/2010 | Durcan |
| 7,833,597 B2 | | 11/2010 | Bavaro et al. |
| 7,862,541 B2 | | 1/2011 | Jeffrey et al. |
| 7,906,066 B2 | | 3/2011 | Wilson et al. |
| 7,951,259 B2 | | 5/2011 | Duchamp et al. |
| 7,967,781 B2 | | 6/2011 | Simpson et al. |
| 7,967,836 B2 | | 6/2011 | Warnack et al. |
| 8,048,058 B2 | | 11/2011 | Fulford |
| 8,052,638 B2 | | 11/2011 | Lee et al. |
| 8,057,430 B2 | | 11/2011 | Grovender et al. |
| 8,251,949 B2 | | 8/2012 | Warnack |
| 8,382,738 B2 | | 2/2013 | Simpson et al. |
| 8,394,055 B2 | | 3/2013 | Durcan |
| 8,444,608 B2 | | 5/2013 | Haslinger et al. |
| 8,444,802 B2 | | 5/2013 | Lee et al. |
| 8,637,132 B2 | | 1/2014 | Bavaro et al. |
| 8,834,510 B2 | | 9/2014 | Wilson et al. |
| 8,840,743 B2 | | 9/2014 | Wantink et al. |
| 9,132,259 B2 | | 9/2015 | Lin et al. |
| 2002/0072705 A1 | * | 6/2002 | Vrba ............... A61F 2/958 604/96.01 |
| 2003/0125709 A1 | | 7/2003 | Eidenschink |
| 2003/0135231 A1 | | 7/2003 | Goodin et al. |
| 2004/0082935 A1 | | 4/2004 | Lee et al. |
| 2005/0070847 A1 | | 3/2005 | van Erp et al. |
| 2005/0261725 A1 | | 11/2005 | Crawford et al. |
| 2006/0135909 A1 | | 6/2006 | Holman et al. |
| 2007/0021772 A1 | | 1/2007 | Von Oepen et al. |
| 2007/0173919 A1 | | 7/2007 | Maschke |
| 2008/0015499 A1 | | 1/2008 | Warnack |
| 2008/0077085 A1 | | 3/2008 | Eidenschink et al. |
| 2008/0125707 A1 | | 5/2008 | Wilson et al. |
| 2009/0036829 A1 | | 2/2009 | Pagel et al. |
| 2009/0171281 A1 | | 7/2009 | Pipenhagen et al. |
| 2009/0223624 A1 | | 9/2009 | Lee et al. |
| 2010/0130925 A1 | | 5/2010 | Haslinger et al. |
| 2010/0189876 A1 | | 7/2010 | Kokish et al. |
| 2010/0217234 A1 | | 8/2010 | Grovender |
| 2010/0285085 A1 | | 11/2010 | Stankus et al. |
| 2011/0022150 A1 | | 1/2011 | Durcan |
| 2011/0060276 A1 | | 3/2011 | Schaeffer et al. |
| 2011/0070355 A1 | | 3/2011 | Bavaro et al. |
| 2011/0160834 A1 | | 6/2011 | Aggerholm |
| 2011/0172696 A1 | | 7/2011 | Jeffrey et al. |
| 2012/0065718 A1 | | 3/2012 | Simpson et al. |
| 2012/0226229 A1 | | 9/2012 | Watanabe et al. |
| 2012/0302952 A1 | | 11/2012 | Kitada et al. |
| 2012/0302994 A1 | * | 11/2012 | Wilson ............... A61M 25/1006 604/506 |
| 2012/0303054 A1 | * | 11/2012 | Wilson ............... A61M 25/0009 606/194 |
| 2013/0178795 A1 | | 7/2013 | Wilson et al. |
| 2014/0276401 A1 | | 9/2014 | Lee et al. |

FOREIGN PATENT DOCUMENTS

| | | |
|---|---|---|
| JP | 2001-333984 A | 12/2001 |
| JP | 2008-237844 A | 10/2008 |
| WO | WO 01/43944 A1 | 6/2001 |
| WO | WO 03/037418 A2 | 5/2003 |
| WO | WO 2008/005706 A2 | 1/2008 |
| WO | WO 2012/162651 A1 | 11/2012 |

OTHER PUBLICATIONS

U.S. Appl. No. 14/458,327, filed Aug. 13, 2014.
U.S. Appl. No. 14/843,308, filed Sep. 2, 2015.
U.S. Appl. No. 13/481,441, Aug. 13, 2014 Issue Fee payment.
U.S. Appl. No. 13/481,441, Jun. 18, 2014 Notice of Allowance.
U.S. Appl. No. 13/481,441, Apr. 18, 2014 Response to Non-Final Office Action.
U.S. Appl. No. 13/481,441, Dec. 18, 2013 Non-Final Office Action.
U.S. Appl. No. 13/481,441, Sep. 12, 2013 Response to Restriction Requirement.
U.S. Appl. No. 13/481,441, Aug. 15, 2013 Restriction Requirement.
U.S. Appl. No. 14/458,327, Nov. 14, 2016 Response to Restriction Requirement.
U.S. Appl. No. 14/458,327, Sep. 13, 2016 Restriction Requirement Filed.
International Search Report for PCT/US2012/039678, dated Sep. 21, 2012 (Corresponds to U.S. Appl. No. 13/481,441 ).
European Search Report dated Jan. 29, 2016 in EP Application No. 15183531.
Partial European Search Report dated Jan. 29, 2016 in EP Application No. 15183539.
U.S. Appl. No. 14/843,074 (US 2016/0339211), filed Sep. 2, 2015 (Nov. 24, 2016).
U.S. Appl. No. 14/458,327, Dec. 5, 2016 Notice of Allowance.
European Search Report dated Oct. 13, 2016 in Application No. EP 15183533.
European Search Report dated Oct. 14, 2016 in Application No. EP 15183534.
U.S. Appl. No. 15/449,462, filed Mar. 3, 2017.
U.S. Appl. No. 14/458,327, Mar. 3, 2017 Issue Fee Payment.
U.S. Appl. No. 14/843,308, Apr. 4, 2017 Non-Final Office Action.
U.S. Appl. No. 14/843,372, Apr. 4, 2017 Non-Final Office Action.
U.S. Appl. No. 14/843,372, filed Sep. 2, 2015.
U.S. Appl. No. 14/843,308, Aug. 4, 2017 Response to Non-Final Office Action.
U.S. Appl. No. 14/843,074, Jun. 5, 2017 Non-Final Office Action.
U.S. Appl. No. 14/843,372, Aug. 4, 2017 Response to Non-Final Office Action.

(56) References Cited

OTHER PUBLICATIONS

U.S. Appl. No. 14/843,308, Nov. 17, 2017 Final Office Action.
U.S. Appl. No. 14/843,372, Nov. 21, 2017 Final Office Action.
U.S. Appl. No. 14/843,074, Nov. 22, 2017 Final Office Action.
U.S. Appl. No. 14/843,074, Oct. 5, 2017 Response to Non-Final Office Action.

* cited by examiner

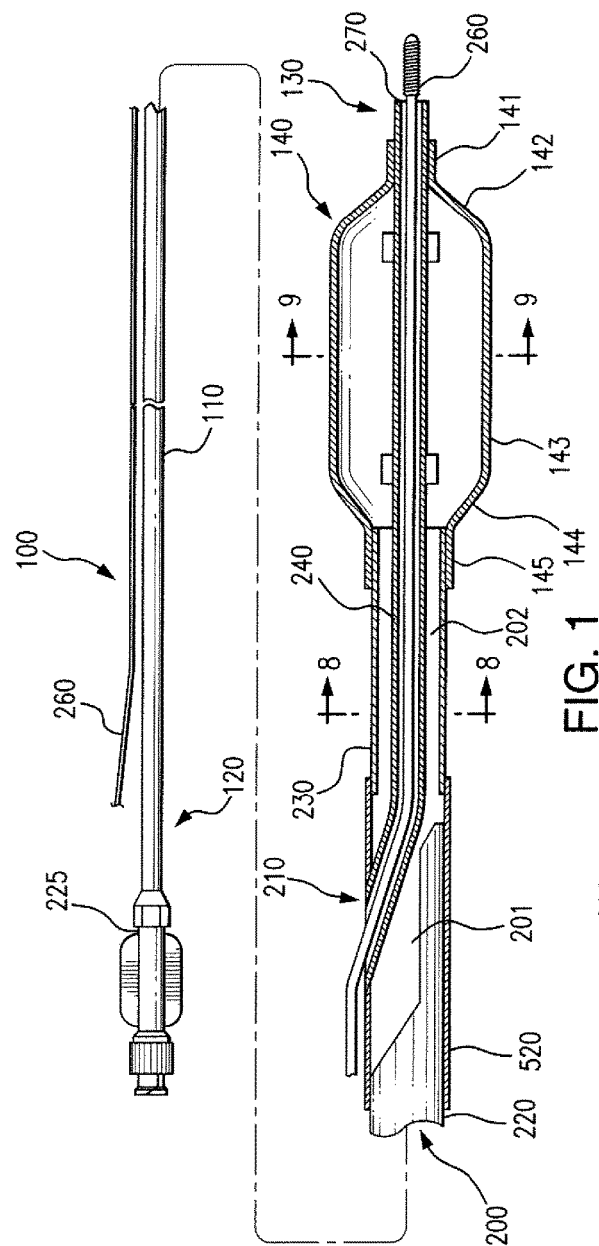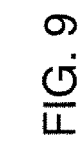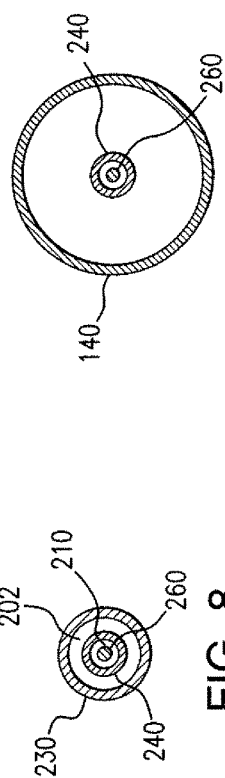

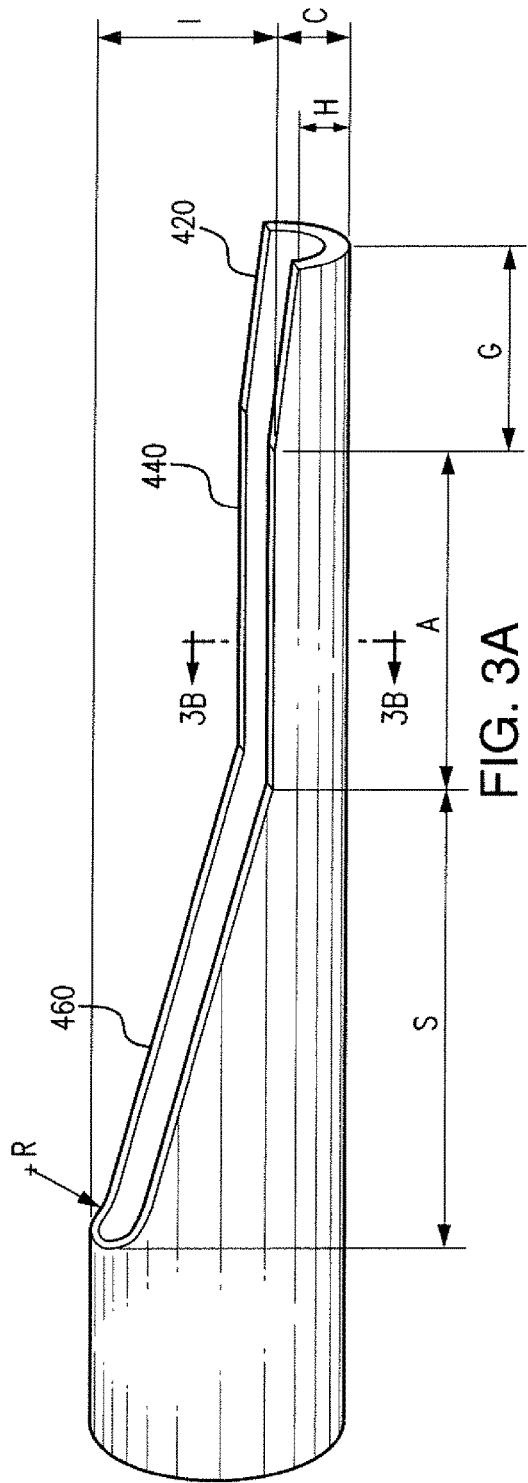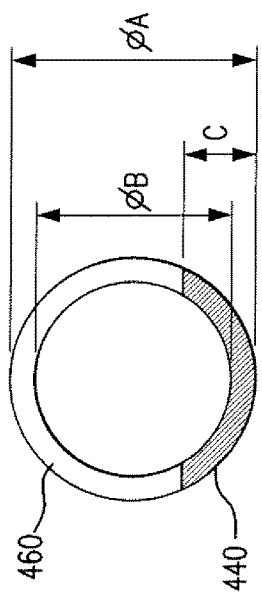
FIG. 3A
FIG. 3B

BALLOON CATHETER

REFERENCE TO RELATED APPLICATIONS

This application claims priority to U.S. Provisional Patent Application No. 62/046,157, filed on Sep. 4, 2014, the contents of which is hereby incorporated by reference in its entirety.

BACKGROUND

Field of the Disclosed Subject Matter

The present disclosed subject matter relates to medical devices, and particularly to intracorporeal devices for therapeutic or diagnostic uses, such as balloon catheters.

Description of Related Subject Matter

In percutaneous transluminal coronary angioplasty (PTCA) procedures, a guiding catheter is advanced in the vasculature of a patient until the distal tip of the guiding catheter is seated in a desired coronary artery. A guidewire is advanced out of the distal end of the guiding catheter into the coronary artery until the distal end of the guidewire crosses a lesion to be dilated. A dilatation catheter, having an inflatable balloon on the distal portion thereof, is advanced into the coronary anatomy over the previously introduced guidewire until the balloon of the dilatation catheter is positioned across the lesion. Once positioned, the dilatation balloon is inflated with inflation fluid one or more times to a predetermined size at a suitable pressure to compress the stenosis against the arterial wall to open up the vascular passageway. Generally, the inflated diameter of the balloon is approximately the same diameter as the native diameter of the body lumen being dilated to complete the dilatation but not over expand the artery wall. After the balloon is deflated, blood resumes flowing through the dilated artery and the dilatation catheter and the guidewire can be removed therefrom.

In such angioplasty procedures, there may be restenosis of the artery, i.e., reformation of the arterial blockage, which necessitates either another angioplasty procedure, or some other method of repairing or strengthening the dilated area. To reduce the restenosis rate and to strengthen the dilated area, physicians may additionally or alternatively implant an intravascular prosthesis inside the artery at the site of the lesion. Such stents may be bare metal, polymeric, or coated with a drug or other therapeutic agent. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter and expanded to a larger diameter by expansion of the balloon. The balloon is deflated to remove the catheter with the stent implanted within the artery at the site of the dilated lesion. Coverings on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as polyester, expanded polytetrafluoroethylene, and DACRON® may be implanted in vessels to strengthen or repair the vessel, or used in an anastomosis procedure to connect vessels segments together. For details of example stents, see for example, U.S. Pat. No. 5,507,768 to Lau, et al. and U.S. Pat. No. 5,458,615 to Klemm, et al., the contents of each of which are incorporated herein by reference in their entireties.

In addition to percutaneous transluminal angioplasty (PTA), PTCA, and atherectomy procedures, balloon catheters are also used to treat the peripheral system such as in the veins system or the like. For instance, a balloon catheter is initially advanced over a guidewire to position the balloon adjacent a stenotic lesion. Once in place, the balloon is then inflated, and the restriction of the vessel is opened. Likewise, balloon catheters are also used for treatment of other luminal systems throughout the body.

Typically, balloon catheters comprise a hollow catheter shaft with a balloon secured at a distal end. The interior of the balloon is in a fluid flow relation with an inflation lumen extending along a length of the shaft. Fluid under pressure can thereby be supplied to the interior of the balloon through the inflation lumen. To position the balloon at the stenosed region, the catheter shaft is designed to have suitable pushability (i.e., the ability to transmit force along the length of the catheter), trackability, and flexibility, to be readily advanceable within the tortuous anatomy of the vasculature. The catheter is also designed so that it can be withdrawn from the patient after delivery. Conventional balloon catheters for intravascular procedures, such as angioplasty and stent delivery, frequently have a relatively stiff proximal shaft section to facilitate advancement of the catheter within the body lumen and a relatively flexible distal shaft section to facilitate passage through tortuous anatomy, such as distal coronary and neurological arteries, without damage to the vessel wall or damage to the stent, in the case of stent delivery.

Traditional catheter shafts are often constructed with inner and outer member tubing separately with an annular space therebetween for balloon inflation. In the design of catheter shafts, it is desirable to predetermine or control characteristics such as strength, stiffness and flexibility of various sections of the catheter shaft to provide the desired catheter performance. This is conventionally performed by combining separate lengths of tubular members of different material and/or dimensions and then assembling the separate members into a single shaft length. However, the transition between sections of different stiffness or material can be a cause of undesirable kinking along the length of the catheter. Such kinking is particularly evident in rapid exchange (RX) catheters, wherein the proximal shaft section does not include the additional structure of a guidewire lumen tube. For example, a conventional RX catheter generally consists of a proximal hypotube having a single inflation lumen therethrough and a dual lumen or coaxial tube configuration at a distal end section having both a guidewire lumen and an inflation lumen therein. Known techniques to minimize kinking at the transition between the more rigid proximal section and the more flexible distal section include bonding two or more segments of materials having different flexibility together to form the shaft. Such transition bonds need to be sufficiently strong to withstand the pulling and pushing forces on the shaft during use.

To address the described issues, catheters having varied flexibility and/or stiffness have been developed with various sections of the catheter shaft that are specifically tailored to provide the desired catheter performance. For example, each of U.S. Pat. No. 4,782,834 to Maguire and U.S. Pat. No. 5,370,655 to Burns discloses a catheter having sections along its length which are formed from materials having a different stiffness; U.S. Pat. No. 4,976,690 to Solar discloses a catheter having an intermediate waist portion which provides increased flexibility along the catheter shaft; U.S. Pat. No. 5,423,754 to Cornelius discloses a catheter having a greater flexibility at its distal portion due to both a material and dimensional transition in the shaft; U.S. Pat. No. 5,649,909 to Cornelius discloses a catheter having a proximal portion with greater stiffness due to the application of a polymeric coating thereto; and U.S. Pat. No. 8,444,608 to Haslinger discloses a multilayer catheter shaft using a combination of a high Shore D durometer value material and a lower Shore D durometer value material to reduce kinking, the contents of each of which are incorporated herein by reference in their entireties.

However, one difficulty has been balancing the often competing characteristics of strength and flexibility of the catheter shaft. Another difficultly has been providing a flexibility transition which improves catheter maneuverability, yet with a sufficiently strong transition bond. Kinking has also been a known issue for over-the-wire (OTW) catheters as well.

As such, there remains a need for a catheter having a shaft with an improved combination of characteristics such as strength, flexibility and ease of manufacture. There is also a need for a catheter that has improved trackability to facilitate further passage through tortuous anatomy, such as distal coronary and neurological arteries, while maintaining the ability to withdraw from the tortuous anatomy.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve the above and other advantages and in accordance with the purpose of the disclosed subject matter, as embodied and broadly described, the disclosed subject matter includes catheters and methods of making a catheter. An exemplary catheter includes an outer shaft member having a proximal section and a distal outer member. The outer shaft has an inflation lumen defined therethrough. The catheter also includes a balloon in fluid communication with the inflation lumen. The balloon has a proximal balloon shaft, a proximal cone portion, a working length, a distal cone portion, and a distal balloon shaft. The proximal balloon shaft is coupled to the distal outer member. The catheter also includes a monolithic inner tubular member having guidewire lumen defined therethrough. The monolithic inner tubular member extends from the outer shaft proximal section through the distal outer member and through the balloon to form a tip. The distal balloon shaft has an inner diameter and comprises a distal seal portion coupled to the inner tubular member and a proximal portion free of attachment to the inner tubular member. The length of the proximal portion of the distal balloon shaft is at least about two times the inner diameter of the distal balloon shaft.

In some embodiments, the tip includes a distal exposed portion distal of the distal seal portion of the distal balloon shaft and a proximal portion along the length of the distal seal portion of the distal balloon shaft. The length of the proximal portion of the distal balloon shaft can be about 35% to about 70% the length of the tip. Additionally or alternatively, the length of the proximal portion of the distal balloon shaft can be about 50% to about 120% the length of the distal exposed portion of the tip. Furthermore, the length of the proximal portion of the distal balloon shaft can be about 25% to about 40% of the combined length of the distal balloon shaft and the distal exposed portion of the tip.

In some embodiments, the inner diameter of the distal balloon shaft is about 0.68 mm to about 0.87 mm. The length of the proximal portion of the distal balloon shaft can be at least about 1.4 mm, preferably about 1.9 mm. The length of the distal seal portion of the distal balloon shaft can be about 1.4 mm. The length of the tip is about 3.0 mm to about 5.0 mm. The length of the distal exposed portion of tip can be about 1.6 mm to about 3.6 mm.

In some embodiments, the distal outer member includes a single layer of polyether block amide. The distal outer member can be necked to a reduced diameter along an entire length of the distal outer member. For example, the reduced diameter can include an outer diameter of about 0.032 inches to about 0.034 inches and/or an inner diameter of about 0.031 inches.

In some embodiments, the proximal section of the outer shaft includes a hypotube having a proximal section and a distal section with the inflation lumen and a longitudinal axis defined therethrough. The distal section of the hypotube can have a skive defined by a first angled cut, an axial cut, and a second angled cut. The first angled cut can have a length of about 100 mm, the axial cut can have a length of about 25 mm, and the second angled cut can have a length of about 25 mm. The axial cut can have a height of about 0.0065 inches to about 0.0075 inches. The second angled cut can define a distal edge height of about 0.0035 inches to about 0.0045 inches. The proximal section of the hypotube can have an outer diameter of about 0.0275 inches to about 0.0285 inches and an inner diameter of about 0.0195 inches to about 0.0205 inches.

In some embodiments, the proximal section of the outer shaft further includes a midshaft member having the guidewire lumen and the inflation lumen defined therethrough. The inflation lumen along the midshaft member can be configured to receive at least a portion of the distal section of the hypotube.

According to another aspect of the disclosed subject matter, methods of making a catheter are provided. An exemplary method includes providing an outer shaft member having a proximal section and a distal outer member. The outer shaft has an inflation lumen defined therethrough. The method also includes providing a balloon in fluid communication with the inflation lumen. The balloon has a proximal balloon shaft, a proximal cone portion, a working length, a distal cone portion, and a distal balloon shaft having an inner diameter. The method includes coupling the proximal balloon shaft to the distal outer member and providing a monolithic inner tubular member having guidewire lumen defined therethrough. The monolithic inner tubular member extends from the outer shaft proximal section through the distal outer member and through the balloon to form a tip. The method also includes coupling a distal seal portion of the distal balloon shaft to the inner tubular member such that the distal balloon shaft includes a proximal portion free of attachment to the inner tubular member. The length of the proximal portion of the distal balloon shaft is at least about two times the inner diameter of the distal balloon shaft.

In some embodiments, the method also includes necking the distal outer member from a first outer diameter of about 0.041 inches to a reduced outer diameter of about 0.032 inches to about 0.034 inches along an entire length of the distal outer member. The distal outer member can have a first inner diameter of about 0.033 inches before necking and a reduced inner diameter of about 0.031 inches along an entire length of the distal outer member after necking.

According to another aspect of the disclosed subject matter, an exemplary catheter includes an outer shaft member having a proximal section and a distal outer member, and the outer shaft has an inflation lumen defined therethrough. The distal outer member includes a single layer of polyether block amide necked to a reduced diameter along an entire length of the distal outer member. The catheter also includes a balloon in fluid communication with the inflation lumen. The balloon has a proximal balloon shaft, a proximal cone portion, a working length, a distal cone portion, and a distal balloon shaft. The proximal balloon shaft is coupled to the distal outer member. The catheter also includes a monolithic inner tubular member having guidewire lumen defined therethrough. The monolithic inner tubular member extends from the outer shaft proximal section through the distal outer member and through the balloon to form a tip. The distal balloon shaft has an inner diameter and includes a distal seal portion coupled to the inner tubular member and a proximal portion free of attachment to the inner tubular member. The length of the proximal portion of the distal balloon shaft is at least about two times the inner diameter of the distal balloon shaft. The proximal section of the outer shaft includes a hypotube having a proximal section and a distal section with the inflation lumen and a longitudinal axis defined therethrough. The distal section of the hypotube includes a skive defined by a first angled cut, an axial cut, and a second angled cut.

It is to be understood that both the foregoing general description and the following detailed description are exemplary and are intended to provide further explanation of the disclosed subject matter claimed. The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTION OF THE DRAWINGS

FIG. 1 is a side view, partially in section, of a balloon catheter embodying features of the disclosed subject matter.

FIG. 3A is a detailed perspective view of the skive at the distal section of the hypotube according to embodiments of the disclosed subject matter.

FIG. 3B is a cross section of the hypotube at section 3B-3B in FIG. 3A.

FIGS. 8 and 9 are transverse cross sectional schematic views of the balloon catheter shown in FIG. 1, taken along lines 8-8 and 9-9, respectively.

DETAILED DESCRIPTION

Figure 2:
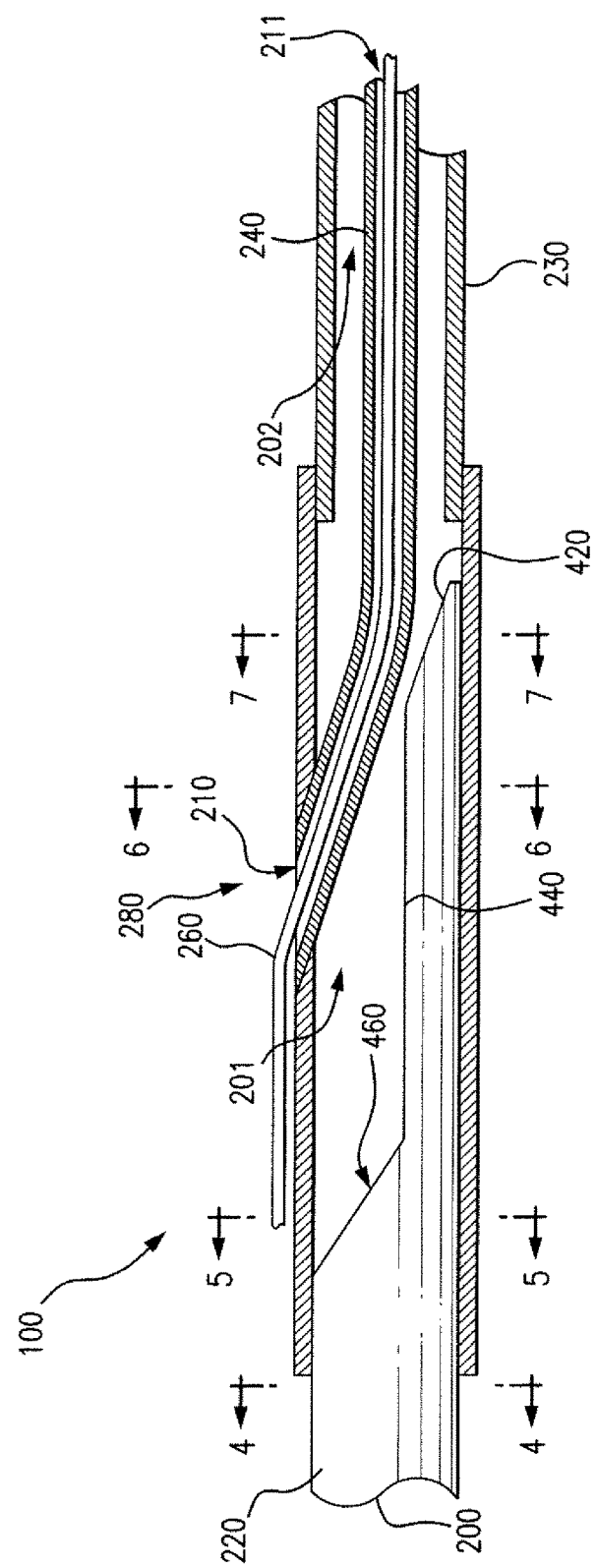
FIG. 2 is a detailed side cross section of the transition region, including the skived distal end of the catheter hypotube disposed within the inflation lumen of a midshaft section and extending into a portion of the inflation lumen of the distal shaft member.

Reference will now be made in detail to various exemplary embodiments of the disclosed subject matter, examples of which are illustrated in the accompanying drawings. The examples are not intended to limit the scope of the disclosed subject matter in any manner. The disclosed subject matter will be described in conjunction with the detailed description of the system.

In accordance the disclosed subject matter, a balloon catheter is provided. The balloon catheter includes an outer shaft member having a proximal section and a distal outer member. The outer shaft has an inflation lumen defined therethrough. The catheter also includes a balloon in fluid communication with the inflation lumen. The balloon has a proximal balloon shaft, a proximal cone portion, a working length, a distal cone portion, and a distal balloon shaft. The proximal balloon shaft is coupled to the distal outer member. The catheter also includes a monolithic inner tubular member having guidewire lumen defined therethrough. The monolithic inner tubular member extends from the outer shaft proximal section through the distal outer member and through the balloon to form a tip. The distal balloon shaft has an inner diameter and comprises a distal seal portion coupled to the inner tubular member and a proximal portion free of attachment to the inner tubular member. The length of the proximal portion of the distal balloon shaft is at least about two times the inner diameter of the distal balloon shaft.

The accompanying figures, where like reference numerals refer to identical or functionally similar elements throughout the separate views, serve to further illustrate various embodiments and to explain various principles and advantages all in accordance with the disclosed subject matter. For purpose of explanation and illustration, and not limitation, exemplary embodiments of the balloon catheter, and method of making thereof, in accordance with the disclosed subject matter are shown in FIGS. 1-21. While the present disclosed subject matter is described with respect to coronary indications, one skilled in the art will recognize that the disclosed subject matter is not limited to the illustrative embodiments, and that the product and methods described herein can be used in any suitable application.

For purpose of illustration, and not limitation, reference is made to an exemplary embodiment of a rapid exchange balloon dilatation catheter 100 shown in FIG. 1. As shown in FIG. 1, the balloon catheter 100 generally comprises an elongated catheter shaft 110 having a proximal shaft section 120 and a distal shaft section 130. The catheter shaft 110 can have a variety of suitable configurations. For example, although depicted as multiple tubes joined together, as discussed herein, certain portions can be formed as single monolithic members as desired. The shaft 110 has an inflation lumen 200, 201, 202 defined therein and a guidewire lumen 210, 211 defined through at least a portion of the shaft 110.

As illustrated in FIG. 1, the proximal shaft section 120 can include a single lumen hypotube 220 or similar tubular member of suitable rigidity and pushability. For example, the hypotube 220 can be a single piece construction tubular member. The hypotube 220 can have a proximal section and a distal section with an inflation lumen 200 and a longitudinal axis defined therethrough. The inflation lumen 200 of the hypotube 220 can comprise any suitable configuration, such as a substantially circular configuration as shown in FIG. 1.

In accordance with the disclosed subject matter, the distal section of the hypotube 220 can have a skive, which is a cut section of the hypotube that gradually reduces in dimension distally along its length. For example, as illustrated in FIGS. 1 and 2, the hypotube 220 can be skived at its distal section with a stepped configuration. The stepped skive in accordance with the disclosed subject matter can improve the pushability (e.g., push force transmission) and resistance to kinking (e.g., by reducing kink points) of the catheter by providing a smoother transition between the hypotube and the more distal catheter components (e.g., a midshaft member and distal outer member as further discussed herein). The stepped skive can also provide improved support for the proximal port 280 described herein.

In some embodiments of the disclosed subject matter, as depicted in FIG. 2, the skive of the hypotube 220 has three distinct sections including a first angled cut 420, an axial cut 440, and a second angled cut 460. The hypotube 220 can reduce in cross-sectional dimension distally along the length of the skive. The first angled cut 420 can be at the distal end of the hypotube 220 and the axial cut 440 can be disposed between the first angled cut 420 and the second angled cut 460 at the proximal end of the skive. The first angled cut 420 can come to a point at the extreme distal end of the skive/hypotube, as depicted in FIG. 2, or the distal end of the hypotube can include a blunt end as depicted in FIG. 3A. Other similar stepped configurations are contemplated.

In some embodiments, the first angled cut 420 and second angled cut 460 each can have a linear or straight angled configuration as depicted herein, or can be curved, such as a parabolic like curve. The first angled cut 420 and the second angled cut 460 can have the same angle of inclination or can have different angles of inclination. As depicted in FIG. 2, for purposes of illustration, the first angled cut 420 and the second angled cut 460 can be substantially parallel with each other. In other embodiments, the first angled cut 420 extends at a first angle relative the longitudinal axis of the hypotube 220 and the second angled 460 cut extends at a second angle relative the longitudinal axis of the hypotube 220 such that the first angle is different from the second angle. For example, but without limitation, angle 460 can be steeper than angle 420. In some embodiments, the angle for 420 is about 0.020° and the angle for 460 is approx. 0.3°. Preferably, the angles should be shallow (e.g., close to 0) to provide improved force transmission and reduce the chance of kinking.

As embodied herein, the first angled cut 420, the axial cut 440, and the second angled cut 460 can have the same or varying lengths, although the overall dimensions can preferably correspond with dimensions of the midshaft member 520 as described further below. For the purpose of illustration, FIGS. 3A and 3B depict schematics of the distal section of the hypotube 220 for a coronary balloon dilation catheter, wherein the hypotube 220 has the first angled cut 420, the axial cut 440, and the second angled cut 460. In the example of FIGS. 3A and 3B, the first angled cut 420 has an axial length G between about 20 mm and about 30 mm, preferably about 25 mm. The first angled cut 420 of this embodiment has a blunt end which can have a distal height H ranging between about 5% to about 25% of the outer diameter of the hypotube 220. In some embodiments, the height H can be about 0.0025 inches to about 0.0065 inches, preferably about 0.0035 inches to about 0.0045 inches.

As shown in FIG. 3A, the axial cut 440 can have an axial length A ranging between about 10 mm and about 40 mm, preferably about 25 mm. The axial cut 440 can have a height C, as depicted in FIG. 3A, that ranges between about 20% to about 50% of the outer diameter of the hypotube 220. For example, the height C ranges between about 0.0060 inches and about 0.0110 inches, preferably about 0.0065 inches to about 0.0075 inches.

For the purpose of illustration, FIG. 3B is a cross-section of FIG. 3A along the lines 3B-3B. FIG. 3B depicts the outside diameter $Ø_A$ and the inside diameter $Ø_B$ of the hypotube 220. In accordance with some embodiments of the disclosed subject matter, the skived hypotube 220 can have increased dimensions so as to form a thicker structure than previously described. For example, an increased thickness dimension can further improve push and kink resistance. For example, the inside diameter $Ø_B$ of the hypotube 220 can be about 0.0195 inches to about 0.0220 inches, preferably 0.0195 inches to about 0.0205 inches. The outside diameter $Ø_A$ of the hypotube 220 can be about 0.0260 inches to about 0.0285 inches, preferably about 0.0275 inches to about 0.0285 inches. The wall thickness of hypotube 220 can be between about 0.0030 inches and about 0.0090 inches, preferably about 0.0080 inches.

As illustrated in FIG. 3A, the second angled cut 460 can have an overall height I when measured from a side of between about 50% to about 90% of the outer diameter of the hypotube 220, preferably about 85%. For example, the height I can about 0.021 inch for a 0.025 inch diameter hypotube. The second angled cut 460 can have an axial length S of about 95 mm to about 105 mm, preferably about 98 mm to about 102 mm, for example about 100 mm. FIG. 3B further depicts the height C of the axial cut 440 in relation to the outside diameter $Ø_A$ and the inside diameter $Ø_B$.

Additionally, an end of one or more cuts can be radiused for transition purposes. For example, and as depicted in FIG.

3A, a proximal end of the second angled cut 460 can comprise a curved or radiused portion. The second angled cut 460 depicted herein includes a radius of approximately 0.040 inches plus or minus about 0.010 inches. In the embodiment of FIG. 3A, the overall axial length of the skive with respect to the first angled cut 420, the axial cut 440, and the second angled cut 460 can range from about 100 mm to about 200 mm. Additional suitable dimensions of the skive are contemplated. Additional features of a skived hypotube can be found in U.S. Patent Publication No. 2012/0303054, which is incorporated by reference herein in its entirety.

In accordance with the disclosed subject matter, the catheter 100 can further include a midshaft section. As depicted in FIG. 2 for purpose of illustration, the midshaft section of the catheter 100 can include a tubular midshaft member 520. The midshaft member 520 includes a guidewire lumen 210 and an inflation lumen 201 defined therethrough. The inflation lumen 201 of the midshaft member 520 is in fluid communication with the inflation lumen 200 of the hypotube 220. Furthermore, at least a portion of the distal section of the hypotube 220 is disposed within the inflation lumen 201 of the midshaft member 520 with the inflation lumen 200 of the hypotube 220 in fluid communication with the inflation lumen 201 of the midshaft member 520. The inflation lumen 201 of the midshaft member 520 depicted herein comprises a generally crescent configuration at a proximal section thereof and the hypotube 220 is inserted into the inflation lumen 201, as further discussed herein.

As embodied herein and as illustrated in FIG. 2, an exterior surface of the midshaft member 520 can define a proximal port 280. The proximal port 280 is spaced distally from the proximal end of the catheter 100. The proximal port 280 is configured to receive a guidewire 260 therethrough and is in communication with the guidewire lumen 210 of the midshaft member 520. In some embodiments, the proximal port 280 is reinforced by the distal section of the hypotube 220 and the distal section of the hypotube 220 is disposed proximate the proximal port 280 of the midshaft member 520. In some embodiments, at least a portion of the axial cut 440 is disposed proximate to the proximal port 280 of the guidewire lumen 210. The location of the proximal port 280 can depend upon various factors, such as the size of the balloon 140, as further discussed herein. In some embodiments, second angled cut 460 is proximal the proximal port 280, the axial cut 440 begins proximal the proximal port 280 and continues distal of the port 280 and first angled cut 420 is located distal of proximal port 280 and extends into a region where the outer member and the inner tubular member are coaxial.

Figure 4:
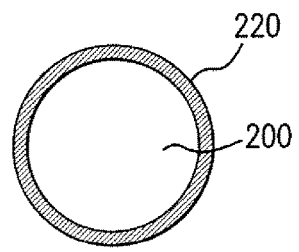
FIGS. 4, 5, 6, and 7 are transverse cross sectional schematic views of the balloon catheter shown in FIG. 2, taken along lines 4-4, 5-5, 6-6, and 7-7, respectively.
Figure 5:
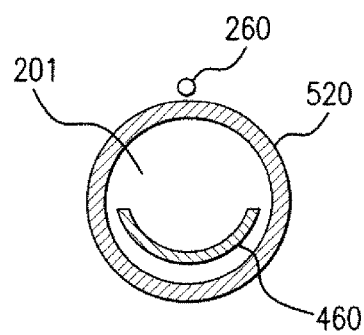

For purpose of illustration and not limitation, FIG. 4 is a cross-section of the catheter 100 of FIG. 2 along the lines 4-4. As depicted in FIG. 4, the hypotube 220 at this section is a single lumen member defining the inflation lumen 200 therethrough with a circular cross section. FIG. 5 is a cross-section of the catheter 100 of FIG. 2 along the lines 5-5. In FIG. 5, the inflation lumen 201 of the midshaft member 520 includes a substantially circular cross section. The inflation lumen 200 of the hypotube 220 is fluidly connected to the lumen 201 of the midshaft member 520. As depicted in FIG. 5, the second angled cut 460 is disposed within the inflation lumen 201 of the midshaft member 520, as further discussed herein.

Figure 6:
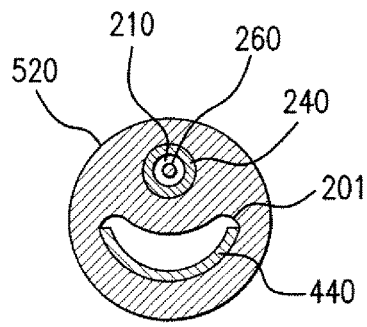

For purpose of illustration, FIG. 6 is a cross-section of the catheter 100 of FIG. 2 along the lines 6-6. The midshaft member 520 at 6-6 includes a crescent like cross section for the inflation lumen 201. With respect to FIGS. 5 and 6, the inflation lumen 201 of the midshaft member 520 transitions from a circular cross section at FIG. 5 to a crescent like cross section at FIG. 6. The transition of the circular cross section of the midshaft member 520 to the crescent like cross section of the midshaft member 520 allows for a smooth transition in flow, as described further herein. The crescent like cross section of inflation lumen 201 can provide for a catheter with a reduced profile as compared to a catheter having a round inflation lumen at locations proximate the proximal port 280.

As depicted in the cross section of FIG. 6, the axial cut 440 can be disposed at least partially in the crescent inflation lumen 201. The space around (e.g., above) the axial cut 440 can define the volume for inflation fluid flow. The corners of the crescent or "smiley" configuration can be rounded or otherwise provided in any suitable shape.

Figure 7:
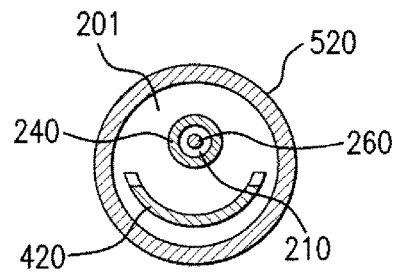

For purpose of illustration and not limitation, FIG. 7 is a cross-section of the catheter 100 of FIG. 2 along the lines 7-7. FIG. 7 depicts a cross section of the midshaft member 520 in which the inflation lumen 201 has transitioned from the crescent configuration to an annular configuration. The first angled cut 420 interfaces with the midshaft member 520 and is positioned adjacent, below as depicted in FIG. 7, the guidewire lumen 210 as defined by inner tubular member 240. The inflation lumen 201 is generally coaxial with the guidewire lumen 210. As depicted FIG. 2, the first angled cut 420 can extend distally beyond the midshaft member 520 into the distal outer member 230.

As depicted in the cross section of the midshaft member 520 shown in FIG. 7, inflation lumen 201 and the guidewire lumen 210 can each have a circular cross-section. Thus, as embodied herein and as shown in FIGS. 4-7, the inflation lumen 200 of the hypotube 220 transitions from a circular cross section at section 4-4 of FIG. 2, to a generally crescent or "smiley" configuration at section 7-7 of the inflation lumen 201 of the midshaft member 520 and then ultimately to a co-axial arrangement at section 7-7. However, the inflation lumen 201 and the guidewire lumen 210 can have alternative cross-sectional shapes as desired.

In accordance with the disclosed subject matter, the skive can serve as a male end section of the hypotube 220 and the inflation lumen 201 of the midshaft member 520 can serve as the female receiving end section. At least a portion of the stepped skive at the distal end section of the hypotube 220 can be configured to be received within the inflation lumen 201 of the midshaft member 520. The skive of hypotube 220 can be disposed within the crescent or smiley shaped inflation lumen to fluidly connect the inflation lumen 200 of the hypotube 220 with the inflation lumen 201 of the midshaft member 520. For example, and as embodied herein the skive portion of the hypotube 220 is disposed within the inflation lumen 201 of the midshaft member 520, as depicted in FIGS. 1 and 6. The axial cut 440 can "float" within inflation lumen 201 and/or interface with a portion of a surface of the inflation lumen 201 of the midshaft member 520. In some embodiments, at least the axial cut 440 can be press fit with the inflation lumen 201 of the midshaft member 520. Furthermore, as embodied herein, the first angled cut 420 is inserted through the inflation lumen 201 of the midshaft section and into the distal shaft section 130, as depicted in FIG. 2. Accordingly, the skive can assist in joining and reinforcing the hypotube 220 with the midshaft member 520, while facilitating a smooth transition in flexibility and reduce kinking of the catheter.

In accordance with the disclosed subject matter, the hypotube 220 can be bonded to midshaft member 520. For example, the distal section of the hypotube 220 can have a roughened outer surface to enhance the bond with the midshaft member 520. The hypotube 220 can be concentrically aligned within the midshaft member 520. Accordingly, the outer diameter or exterior surface of the hypotube 220 can be sized to fit concentrically within the interior surface of the midshaft member 520 at least at a distal section of the hypotube 220 and the hypotube 220 can be bonded to the midshaft member 520 along this portion with the remainder of the hypotube (e.g. including the skive) free of attachments to the midshaft member 520. Alternatively, in some embodiments, the hypotube 220 can be bonded with the midshaft member 520 along the length of the hypotube 220 or at portions along the length of the hypotube 220, as depicted in FIG. 2.

In some embodiments, the hypotube 220 or proximal tubular member can be free of any outer coating or jacket, so as to have a bare exposed outer surface. In this manner, a hypotube 220 of larger cross section can be provided without increasing the profile of the proximal shaft section 120 as compared to a conventional rapid exchange catheters with a coated or jacketed hypotube. For example, the reduction in thickness by omitting a coating can allow for a proportional increase in both the outer diameter and thus the inner diameter of the tubular member. Thus, the overall profile of the catheter along the proximal end section can remain the same, but the dimensions of the inflation lumen therein can be increased. The increase in inner diameter can result in greater fluid flow for increased inflation or deflation (e.g., decreased inflation and deflation times) as compared to conventional catheters with coating having the same overall profile. In some embodiments, a thicker hypotube can be provided that can provide increased strength and pushability without substantially effecting profile and or inflation time as compared to known jacketed hypotubes. Further, the bare hypotube can also result in a better grip and a reduction in kinking.

In accordance with the disclosed subject matter and as depicted in FIG. 2, the distal shaft section 130 of the catheter 100 can include a distal outer member 230 extending distally from the midshaft member 520. The distal outer member 230 is coupled to the midshaft member 520 by at least one of bonding, adhesive, lap joint, and butt joint or by other suitable configurations as known in the art, however, a lap joint formed via heat bonding is preferred.

As embodied herein, the distal outer member 230 can have a guidewire lumen 211 and an inflation lumen 202 defined therein. The guidewire lumen 211 of the distal outer member 230, defined by the inner tubular member 240, can be in fluid communication with the guidewire lumen 210 of the midshaft member 520. The inflation lumen 202 of the distal outer member 230 can be in fluid communication with the inflation lumen 201 of the midshaft member 520.

As depicted in FIG. 2 for illustration, the distal outer member 230 can extend distally from the midshaft member 520. The guidewire lumen 211 can be defined by the inner tubular member 240 extending from the midshaft member 520 through the distal outer member 230. The distal outer member 230 and the inner tubular member 240 define inflation lumen 202 therebetween in fluid communication with the inflation lumen 201 of the midshaft member 520. Thus, a coaxial annular configuration with the inner tubular member 240 positioned within the distal outer member 230 can be provided. Alternatively, the distal outer member can be formed as a dual lumen monolithic member with the guidewire lumen and the inflation lumen defined therein.

For purpose of illustration and not limitation, FIG. 8 is a cross-section of the catheter 100 of FIG. 2 along the lines 8-8. As depicted in FIGS. 1 and 8, the inflation lumen 202 of the distal outer member 230 includes an annular configuration. The inflation lumen 202 is defined by the annular space between the interior surface of the distal outer member 230 and the exterior surface of the inner tubular member 240, although a variety of suitable shaft configurations can alternatively be used including non-coaxial and multi-lumen extrusions. The transition from the circular to crescent to annular shape of the inflation lumens 200, 201, 202 allows for smooth flow without significant back pressure or resistance.

As embodied herein, the catheter shaft 110 includes an inner tubular member 240 that defines the guidewire lumen 210, 211 configured to slidably receive a guidewire 260 therein. In a preferred embodiment, the inner tubular member 240 can comprise one tube (i.e., monolithic and/or zero-transition) such that the inner tubular member 240 forms the tip 270, as described in more detail below. The zero-transition inner tubular member 240 can provide continuous flexibility and direct force transfer, improved crossing of challenging anatomy with less force, and improved tactile feedback. Alternatively, the inner tubular member 240 can be comprised of a plurality of tubes connected together. The inner tubular member 240 can be the same member extending through the midshaft member 520, or can be a separate member connected therein, as known in the art. An exterior surface of the distal outer member 230 can interface with an interior surface of the midshaft member 520 at a distal end section of the midshaft member 520. The midshaft member 520 and the distal outer member 230 can be coupled in a variety of ways including, but not limited to bonding, adhesives, lap joints, butt joints and the like, although a lap joint formed by heat bonding is preferred. The inflation lumen 201 of the midshaft member 520 is fluidly coupled to the inflation lumen 202 of the distal outer member 230 to provide for a path for inflation of the balloon 140, as further discussed herein.

Thus, from the proximal end section to the distal end section, the catheter 100 embodied herein transitions from a single lumen (inflation lumen) configuration in the proximal shaft section 120 to a coaxial dual lumen (inflation lumen and guidewire lumen) configuration in the distal shaft section 130. The midshaft section generally defines the juncture between the single lumen hypotube 220 and the coaxial dual lumen distal shaft section 130.

As depicted in FIG. 1, balloon 140 can be coupled to the distal outer member 230 and is in fluid communication with the inflation lumens 200, 201, and 202. For purpose of illustration and not limitation, FIG. 9 is a cross-section of the catheter 100 of FIG. 1 along the lines 9-9. As depicted in FIGS. 1 and 9, a balloon 140 is sealingly secured to the distal outer member 230 such that an interior of the balloon 140 is in fluid communication with inflation lumens 200, 201, and 202.

Figure 14:
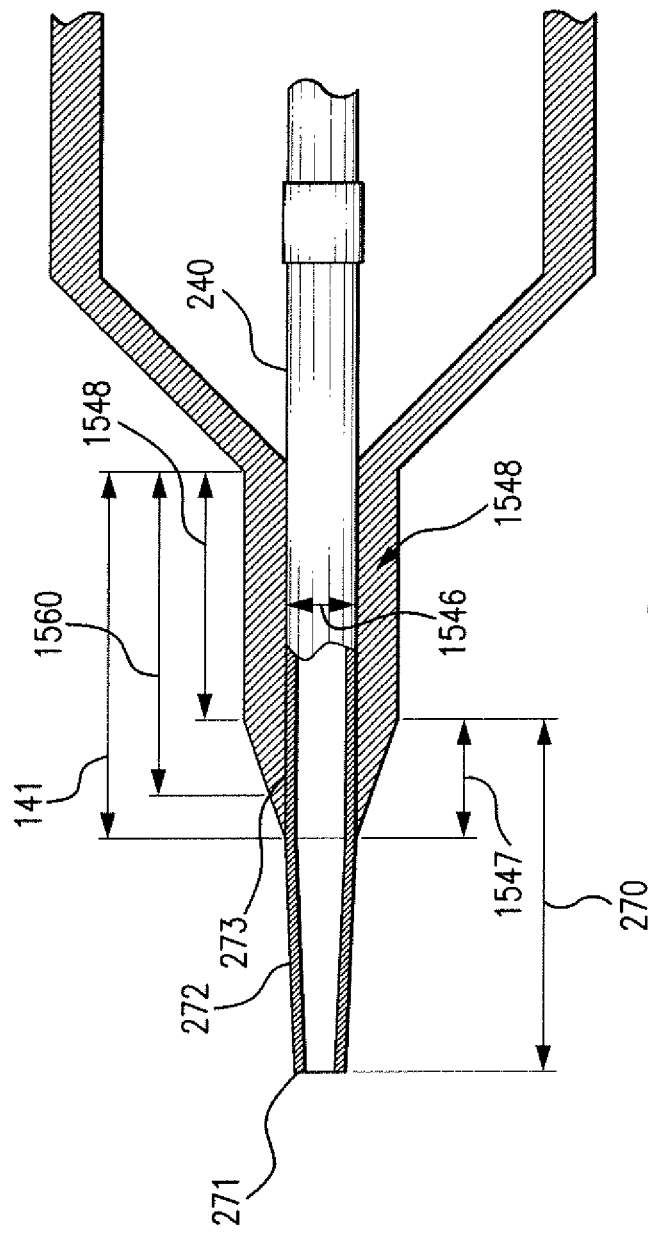
FIG. 14 is a partial side view of an exemplary monolithic inner tubular member forming a tip and a balloon according to embodiments of the disclosed subject matter.

As shown in FIG. 1 for illustration and not limitation, the balloon 140 can have a proximal balloon shaft 145, a proximal cone portion 144, a working length 143, a distal cone portion 142, and a distal balloon shaft 141. The balloon 140 can be coupled to the distal outer member 230 and inner tubular member 240 in any suitable manner. In some embodiments, the balloon 140 is coupled to the distal outer member 230 along a longitudinal length of the proximal balloon shaft 145 and coupled to the inner tubular member 240 along a longitudinal length of the distal balloon shaft 141, as depicted in FIG. 1. For example, the distal balloon shaft 141 can have a distal seal portion 1547 coupled to the inner tubular member 240 and a proximal portion 1548 of the distal balloon shaft free of attachment to the inner tubular member 240 as shown in FIG. 14 for the purpose of illustration and not limitation. The length of the proximal portion 1548 of the distal balloon shaft free of attachment can be at least about two times the inner diameter 1546 of the distal balloon shaft 141.

As embodied herein, the inner tubular member 240 can be a monolith piece that forms the tip 270 of the catheter as shown in FIG. 14 for the purpose of illustration and not limitation. The tip 270 includes a distal exposed portion 272 and a proximal portion 273 along the length of the distal seal portion 1547 of the distal balloon shaft. In some embodiments, the length of the proximal portion 1548 of the distal balloon shaft is about 35% to about 70% the length of the tip 270. Additionally or alternatively, the length of the proximal portion 1548 of the distal balloon shaft can be about 50% to about 120% the length of the distal exposed portion 272 of the tip. Furthermore, the length of the proximal portion 1548 of the distal balloon shaft can be about 25% to about 40% of the combined length of the distal balloon shaft 141 and the distal exposed portion 272 of the tip. In some embodiments, the interior of the balloon 140 can be in fluid communication with the inflation lumen 200, 201, and 202.

In some embodiments, the tip length (including the distal exposed portion 272 and the proximal portion 273) can be about 3.0 mm to about 4.0 mm for 2.0 mm to 3.25 mm balloons and about 4.0 mm to about 5.0 mm for 3.5 mm to 4.0 mm balloons. The distal exposed portion 272 can have a length of about 1.6 mm to about 2.6 mm for 2.0 mm to 3.25 mm balloons and about 2.6 mm to about 3.6 mm for 3.5 mm to 4.0 mm balloons. The proximal portion 273 of the tip can have a length of about 1.4 mm. As discussed herein, the tip can taper distally and define a distal most tip 271 having an outer diameter of up to about 0.020 inches max and inner diameter of about 0.015 inches minimum.

In some embodiments, the distal balloon shaft 141 can have inner and outer diameters that vary based on the size of the balloon: for 2.00 mm balloons, the inner diameter can be about 0.0270 inches and the outer diameter can be about 0.0300 inches; for 2.25 mm balloons, the inner diameter can be about 0.0275 inches and the outer diameter can be about 0.0300 inches; for 2.50 mm balloons, the inner diameter can be about 0.0275 inches and the outer diameter can be about 0.0300 inches; for 2.75 mm balloons, the inner diameter can be about 0.0275 inches and the outer diameter can be about 0.0315 inches; for 3.00 mm balloons, the inner diameter can be about 0.0275 inches and the outer diameter can be about 0.0325 inches; for 3.25 mm balloons, the inner diameter can be about 0.0285 inches and the outer diameter can be about 0.0330 inches; for 3.5 mm balloons, the inner diameter can be about 0.0305 inches and the outer diameter can be about 0.0355 inches; and for 4.0 mm balloons, the inner diameter can be about 0.034 inches and the outer diameter can be about 0.0370 inches.

In some embodiments, the distal balloon shaft 141 can have a trim length 1560 prior to sealing to the inner tubular member 240 of about 2.6 mm to about 2.8 mm. The distal balloon shaft 141 can have a length of about 3.3 mm after sealing to the inner tubular member (e.g., by laser as described herein). The distal seal portion 1547 of the distal balloon shaft can have a length of about 1.4 mm. The proximal portion 1548 of the distal balloon shaft free of attachment to inner tubular member 270 can have a length of about 1.9 mm.

The balloon cone length can vary based on the size of the balloon. For example, for 2.0 mm to 3.00 mm diameter balloons (of any length), the balloon cone length can be 2 mm. For 3.25 mm diameter balloons (of any length), the balloon cone length can be 3 mm. For 3.5 mm diameter balloons having a length of 8 mm or 12 mm, the balloon cone length can be 4 mm. For 4.0 mm diameter balloons having a length of 8 mm or 12 mm, the balloon cone length can be 5 mm. For 3.5 mm to 4.0 mm diameter balloons having a length of 15 mm, 18 mm, 23 mm, 28 mm, 33 mm, or 38 mm, the balloon cone length can be 3 mm. The stent-to-balloon shoulder length can be about 0.651 mm plus or minus 0.107 mm.

Inner tubular member 240 and balloon 140 configurations in accordance with the disclosed subject matter unexpectedly provide for improved trackability, allowing the catheter to advance further within the vascular system of a patient. For example, the length of the proximal portion 1548 of the distal balloon shaft free of attachment to the inner tubular member 240 in accordance with the disclosed subject matter can provide for centering of the catheter (e.g., a coaxial position system) when traversing a bend in the vessel system, providing reduced stent damage as compared to known catheters due to contact with the side of the vessel (e.g., calcified lesions). Furthermore, known catheter systems having a distal balloon shaft entirely bonded to the inner tubular member can have increased stiffness, which can reduce the trackability of the distal portion of the catheter as compared to catheters in accordance with the disclosed subject matter.

In accordance with the disclosed subject matter, the distal balloon shaft 141 of the balloon 140 can be coupled to the inner tubular member 240 in a plurality of suitable ways. For example, the distal balloon shaft 141 can be fusion bonded to the inner tubular member 240, for example, by applying heat to at least a portion of the area of overlap. For illustration and without limitation, electromagnetic energy, such as thermal, laser, or sonic energy can be applied to the distal balloon shaft 141 to bond at least a portion of the distal balloon shaft 141 to the inner tubular member 240. Heating the distal balloon shaft 141 can cause the polymeric material of the distal balloon shaft 141 to soften, or melt and flow, providing a distal seal portion 1547 with a tapered configuration as shown in FIG. 14.

In some embodiments, a heat shrink tubing (not shown) can be positioned around the outside of the distal balloon shaft 141, which can have a trim length of about 2.6 mm to about 2.8 mm prior to melt bonding. The heat shrink tubing, also referred to as a "heat shrink sleeve," can be composed of a polymeric material configured to shrink when exposed to heat. U.S. Pat. No. 7,951,259, which is hereby incorporated by reference in its entirety, discloses the use of a heat shrink sleeve in fabricating a catheter with a flexible distal end. The heat shrink tubing, when heated, shrinks and exerts an inward radial force on the distal balloon shaft 141. With the polymer of the distal balloon shaft 141 in a molten or softened state, the diameter of the distal balloon shaft 141 can be reduced by the force exerted by the heat shrink tubing. After the balloon 140 is cooled, the heat shrink tubing can be removed. Heating can be accomplished, for example, by laser heating (e.g., using a $CO_2$ laser), contact heating (e.g., using aluminum nitride, resistance, RF), hot air, resistance heating, induction heating or the like. As embodied herein, for purposes of illustration and not limitation, a solid state laser can be used to heat the shrink tubing and soften the distal balloon shaft 141. As a result, a portion of the outer surface of the distal balloon shaft 141, in its softened or molten state, can be bonded to the inner tubular member 240. Other catheter connections, such as the proximal balloon shaft 145 to the distal outer member 230 (e.g., via lap joint with proximal balloon shaft 145 over the distal outer member 230) and connections between the various shaft sections (e.g., lap joint of midshaft member 520 over distal outer member 230), can be formed using the fusion bonding methods described herein.

In some embodiments, the exposed portion 272 of the tip can be tapered as shown in FIG. 14 during the same laser bonding process as forming the bond between the distal balloon shaft 141 and the inner tubular member 240 by traversing the laser along the length of the tip 270 and allowing the molten material to flow distally. The tapered flexible tip can provide improved maneuverability to traverse tortuous anatomy. The distal balloon shaft 141 provides an area to seal 1547 the distal end of the balloon 140 to the inner tubular member 240 just proximal to the tip 270. In some embodiments, a smaller length of the seal can provide improved flexibility to the distal section of the catheter but still provide suitable tensile strength. A smaller length of the seal can also reduce heat-induced damage to the balloon cone during the heat bonding process (which could result in rupture) by increasing the distance between the location of the seal and the balloon cone section. According to some embodiments of the disclosed subject matter, the distal balloon shaft 141 can be non-milled. Forming the balloon 140 with a distal seal portion 1547 coupled to the inner tubular member 240 and a proximal portion 1548 free of attachment to the inner tubular member 240 according to the disclosed subject matter can improve catheter trackability through tortuous vasculature or the like.

As depicted in FIG. 1 for the purpose of illustration and not limitation, the balloon 140 can comprise as a single layer of polymer material. However, multilayered balloons are preferred. For example, the balloon 140 can have a first layer made of a first polymer material having a first Shore durometer hardness, and a second layer made of a second polymer having a second Shore durometer hardness. In some embodiments, the first Shore durometer hardness can be greater than the second Shore durometer hardness, and the first layer can be an outer layer relative to the second layer. For example, the balloon 140 can have a first outer layer of polyether block amide (e.g., commercially available as PEBAX®) having a Shore durometer hardness of between about 55 D and about 63 D and a second inner layer of polyether block amide having a Shore durometer hardness of between about 70 D and about 72 D. Preferably, the balloon 140 has a first outer layer of PEBAX® 72 D and a second inner layer of PEBAX® 63 D. Details of suitable multilayer balloons are described in U.S. Pat. No. 7,828,766, U.S. application Ser. No. 12/897,202, and U.S. application Ser. No. 13/680,299, the contents of each of which are herein incorporated by reference in their entirety.

In accordance with the disclosed subject matter, the balloon 140 can be composed of a wide variety of suitable materials, for example, nylons, co-polyamides such as PEBAX®, polyester, co-polyester, polyurethane, polyethylene, or the like. For example, the balloon 140 can be formed of a polymeric material which is compatible with the material forming the outer surface of the shaft, to allow for fusion bonding, although the balloon 140 can alternatively or additionally be adhesively bonded to the shaft. The balloon can have wings and be folded as known in the art. For example, the balloon can have five folds for 2.75 mm to 4.0 mm diameter balloons and three folds for smaller diameter balloons (e.g., 2.0 mm to 2.5 mm diameter balloons). The balloon folds can improve the uniformity of stent deployment.

As embodied herein, the balloon 140 can be a relatively high rupture pressure, non-compliant balloon, which in some embodiments has a rupture pressure of about 20 atm to about 30 atm, such that the balloon 140 can be inflated in the patient during a procedure at relatively high working pressure of about 18 atm. In some embodiments, the balloon 140 has a rated burst pressure of about 14 atm to about 25 atm. In embodiments having a balloon with a first outer layer of PEBAX® 72 D and a second inner layer of PEBAX® 63 D, the rated burst pressure can be about 18 atm and the nominal pressure can be about 10 atm. The rated burst pressure (RBP), calculated from the average rupture pressure, is the pressure at which 99.9% of the balloons can be pressurized to without rupturing, with 95% confidence. Generally, a balloon is inflated in the patient during a procedure at working pressure of about 8 atm to about 18 atm, preferably about 10 atm to about 18 atm. The balloon 140 can be any suitable size known in the art, e.g., 2.00, 2.25, 2.50, 2.75, 3.00, 3.25, 3.50, or 4.00 mm diameter.

Additional suitable materials, configurations, and methods of manufacture of the balloon 140 are provided in U.S. Pat. Nos. 7,074,206, and 8,052,638, each of which is hereby incorporated by reference in its entirety. Additional features proximate the balloon 140 can include markers (e.g., made of platinum/iridium and located both ends of the working length of the balloon), stents, and an atramatic tip (not shown). Examples of such features and additional features include those described in U.S. Pat. No. 7,862,541; U.S. application Ser. No. 12/983,504; U.S. Pat. No. 7,549,975; U.S. application Ser. No. 12/468,745; U.S. Pat. No. 6,964,750; U.S. application Ser. No. 11/455,382; U.S. Pat. No. 7,833,597; U.S. Pat. No. 7,322,959; U.S. Pat. No. 7,303,798; U.S. application Ser. No. 11/775,480; U.S. application Ser. No. 12/945,566; U.S. Publication 2010/0285085; U.S. Publication No. 2010/0189876; U.S. Pat. No. 6,923,822; U.S. application Ser. No. 11/189,536; U.S. Publication No. 2009/0036829; U.S. Publication No. 2007/0021772; U.S. application Ser. No. 11/241,936; and U.S. application Ser. No. 14/212,966, the contents of each of which are herein incorporated by reference in their entirety.

In accordance with the disclose subject matter, the balloon 140 can have a stent or scaffold (not shown) mounted thereon for stent delivery applications. The stent or scaffold can be made of any suitable material. For example, the stent can comprise a cobalt chromium alloy (e.g., L-605 comprising Co—Cr—W—Ni). The stent can have any suitable dimensions (e.g., having rounded struts with a thickness of about 0.0032 inches) and be any suitable length, e.g., 8, 12, 15, 18, 23, 28, 33, or 38 mm. The stent can have any suitable configuration. For example, for 2.0 mm to 3.25 mm stents, the design can have six crests connected by non-linear links. For 3.50 mm to 4.0 mm stents, the stent design can have nine crests connected by non-linear links. The stent design can have a proximal end ring with symmetric crests and bar arms. The degree of recoil of the stent diameter can be about 4.4% for 3.00×18 mm stents at nominal. The stent can have a high radial force above peak arterial pressure of 275 mmHg. In some embodiments, the stent is not prone to longitudinal deformation when an external force is applied to the stent. The maximum circular unsupported area can be about 1.01 mm$^2$ for 3.00×18 mm stents and the maximum circular access diameter (i.e., the largest diameter that can fit through struts) is about 1.13 mm for 3.00×18 mm stents. The metallic surface area to artery ratio can be about 13.3% for 3.00 mm stents and about 12.8% for 4.00 mm stents. Preferably, the stent can have about 0% shortening on expansion. The inner tubular member can include markers along its longitudinal length such that the middle of the markers are longitudinally aligned with the ends of stent to improve placement of the stent at the target site during treatment. The markers can be about 1.0 mm wide for 8 mm to 28 mm stents and can be about 1.5 mm wide for 33 and 38 mm stents. The shaft can also include proximal markers 95 cm and 105 cm proximal of the distal tip.

As embodied herein, the stent can include a drug and/or or polymer coating as known in the art. For example, the stent can include a poly(n-butyl methacrylate) (PBMA) and poly(vinylidene fluoride-co-hexafluoropropylene) (PVDF-HFP) and Everolimus coating. The drug dose can be about 40 μg to about 185 μg depending on the stent diameter and length with a drug load of about 100 μg/cm$^2$. The drug can have an elution profile of about 80% at 30 days and about 100% at 120 days.

As depicted in FIG. 1 for purpose of illustration and not limitation, an adapter 225 (e.g., single arm) and a strain relief can be provided at the proximal end of the catheter 100 for access to the inflation lumens 200, 201, 202 collectively, and can be configured for connecting to an inflation fluid source (not shown). The balloon 140 can be provided at a distal end of the catheter and in fluid communication with the inflation lumens 200, 201, 202. The distal end of the catheter can be advanced to a desired region of a body lumen in a conventional manner and balloon 140 inflated to perform a medical procedure, such as to dilate a stenosis and/or deliver a stent or the like. The catheter 100 is then withdrawn or repositioned for another procedure. FIG. 1 illustrates the balloon 140 inflated.

In accordance with the disclosed subject matter, the catheter components can comprise a variety of suitable materials. For example, the hypotube 220 can be a more rigid material than the material of the midshaft member 520 or the distal outer member 230. In some embodiments, the hypotube 220 can be a relatively high stiffness material including a metal, such as but not limited to stainless steel (e.g., 304), although a high durometer polymer can be used. The midshaft member 520, coupled to the hypotube 220, can be more flexible than the hypotube 220 and can comprise a more flexible material. In some embodiments, the midshaft member 520 comprises nylon (e.g., nylon 12) or other suitable polymeric materials.

In accordance with the disclosed subject matter, the distal outer member 230 can be more flexible than the proximal shaft section 120. For example, but not limitation, the distal outer member 230 can be a single layer and can comprise a polyether block amide (e.g., commercially available as PEBAX®) having as shore Durometer hardness of about 72 D. Alternatively, the distal outer member 230 can comprise other polymers and/or can be a multilayer member made of one or more polymers, such as different Shore durometer hardness of polyamide or polyether block amides.

As embodied herein, the inner tubular member 240 can be a single layer or multilayer member made of one or more polymeric materials. For example, the inner tubular member 240 can comprise outer, inner and intermediate layers. In some embodiments, the outer layer comprises polyether block amide (e.g., PEBAX® 72 D), the inner layer comprises a lubricious polymer (e.g., high density polyethylene (HDPE)), and the intermediate layer comprises a tie material (e.g., ethylene acrylic acid adhesive polymer commercially available as Primacor®).

In accordance with the disclosed subject matter, a rapid exchange proximal port 280 can be formed in the midshaft member 520 or at any other suitable location along the length of the catheter using any technique known in the art. For example, an opening can be formed in the side wall of the midshaft member 520 and the inner tubular member 240 can be inserted through the opening to extend distally within the catheter (e.g., through the midshaft, distal outer member, and balloon). A mandrel or pressurizing fluid can be provided within the guidewire lumen 210 of the inner tubular member 240 to maintain the round shape of the guidewire lumen 210 during bonding, and optionally a shrink wrap can be provided over the midshaft member 520 proximate the opening. The midshaft member 520 can be fusion bonded, for example by heating with a laser, to the inner tubular member 240 within the interior of the midshaft member 520. The crescent shape of the inflation lumen 201 of the midshaft member 520 can be formed during the heating process by positioning a crescent shaped mandrel within the tubular midshaft member 520 proximate the port. The heating process can provide a temperature sufficient to soften or melt the materials of the tubular midshaft member 520 and the inner tubular member 240 to define the lumens therein. Shrink wrap material can be used to maintain the outer shape and dimension of the midshaft member 520 by the fusion process. The mandrel and shrink wrap can then be removed after the fusion or heating process is complete.

Figure 10B:
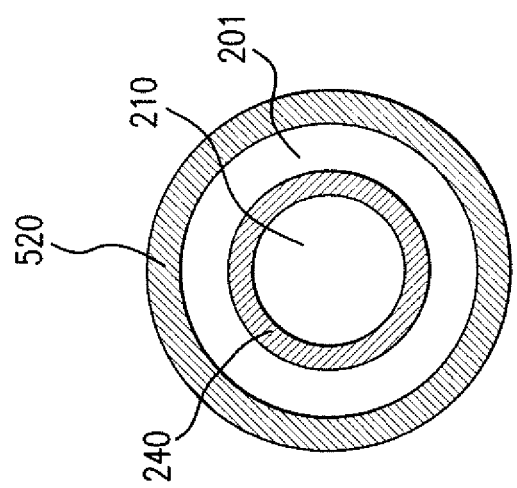
FIGS. 10A and 10B are schematic views of the cross section of the distal shaft section and the midshaft section according to embodiments the disclosed subject matter.
Figure 10A:
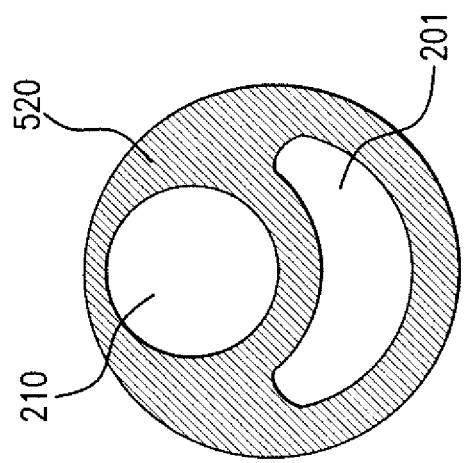

For purpose of illustration and not limitation, FIGS. 10A and 10B depict cross-sections of the midshaft member 520 during manufacture. FIG. 10A depicts the cross section of the midshaft member 520 and inner tubular member 240 of a coaxial configuration, where the guidewire lumen 210 is concentric with the inflation lumen 201, similar to FIG. 8. FIG. 10B depicts a cross-section from the midshaft member 520 after the melting or fusion process depicting the inflation lumen 201 defined by a crescent mandrel. The dual lumen configuration of FIG. 10B can be formed by alternative techniques known in the art. For example, the midshaft member 520 can be molded to include a dual lumen member extending at least a length thereof for purpose of strength and transition from the proximal end section to the distal end section.

Figure 13:
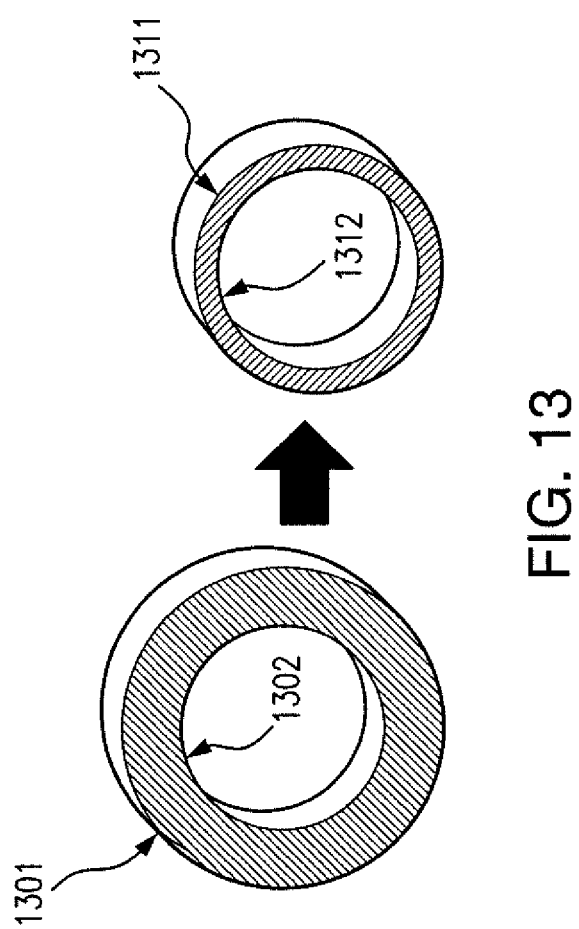
FIG. 13 is a partial cross-sectional view of an exemplary distal outer member prior to and after a necking process according to embodiments of the disclosed subject matter.

As embodied herein, the distal outer member 230 can have a necked portion disposed between its proximal end and its distal end. In a preferred embodiment, the distal outer member 230 is necked along its entire length. The distal outer member 230 can be a single layer necked tubular member comprising any suitable material. For example, the material can be a polyether block amide, commercially available under the trade name PEBAX®. The polyether block can have any suitable hardness, for example a Shore durometer hardness of about 72 D. The distal outer member 230 can be necked by placing an extruded tube in a necking machine, as is known in the art. For example, the necking machine can use a heated die traversing along the length of the extruded tube to reduce the diameter of the distal outer member 230, as shown in FIG. 13 for the purpose of illustration and not limitation. The necked tube can be stabilized at 125° C. for about 10 minutes.

In some embodiments as shown in FIG. 13 for illustration, the diameter of the tube as extruded can be reduced from about 0.041 inch OD (1301 in FIG. 13) and about 0.033 inch ID (1302) to a range of about 0.032 inch to about 0.034 inch OD (1311) and about 0.031 inch ID (1312) via necking. The diameter of the inner diameter can be controlled via the necking process by placing a mandrel of the desired size within the lumen of the extruded tube. According to some embodiments, the distal outer member 230 is necked to a reduced diameter along an entire length of the distal outer member 230. Necking can provide for more reliable dimensions and can introduce orientation into the polymer materials, which can increase the strength of the distal outer member without significantly effecting flexibility. Alternatively, the distal outer member 230 can be necked along a portion of length of the distal outer member 230 to form a taper or step down in diameter. Furthermore, the distal end of distal outer member 230 can be necked to a smaller diameter than the rest of the distal outer member 230 so that the proximal balloon shaft 145 can more easily fit over the distal outer member 230 for heat bonding to a reduce profile.

In accordance with some embodiments of the disclosed subject matter, at least a portion of one or more sections of the catheter can comprise a tubular member formed of a biaxially oriented thermoplastic polymeric material, such as described in U.S. Publication No. 2012/0303054 and U.S. Pat. No. 7,906,066, the contents of each of which are incorporated herein by reference in their entirety. For example, in alternative embodiments of the disclosed subject matter, the distal outer member 230 is formed of the biaxially oriented polymer tubing, which can be single or multilayer. The multilayer construction can, for example, include different durometers of polyamide. It is desired for the rupture strength of the catheter shaft 110 to be greater than that of the balloon 140. As embodied herein, for example, the rated burst pressure of the balloon 140 can be significantly less than (e.g., about 4 atm less than, or about 20% less than) that of the biaxially oriented tubular outer member.

Figure 11:
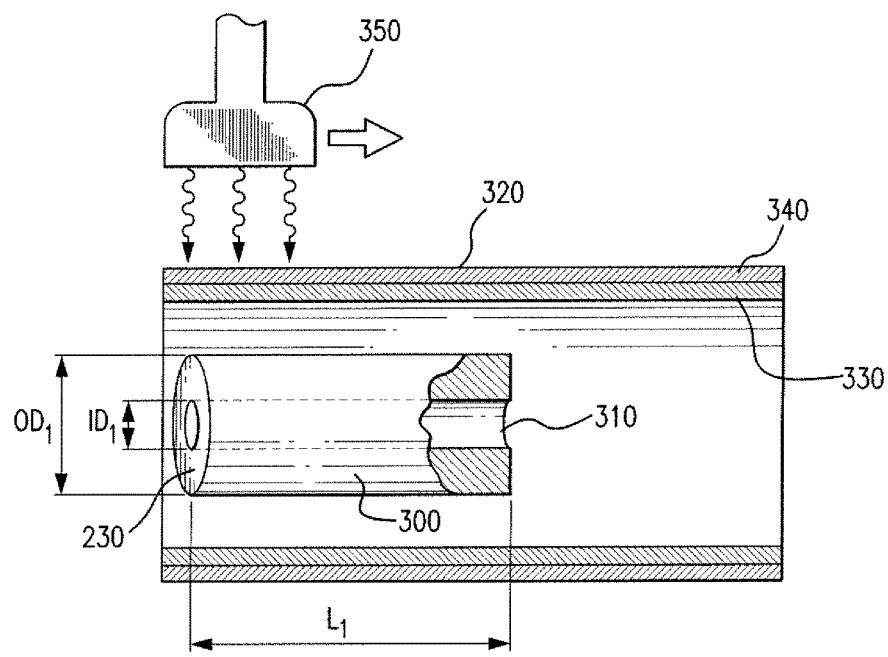
FIG. 11 is a side view in section of a catheter shaft tubular member within a capture member prior to being radially and longitudinally expanded according to some embodiments of the disclosed subject matter.
Figure 12:
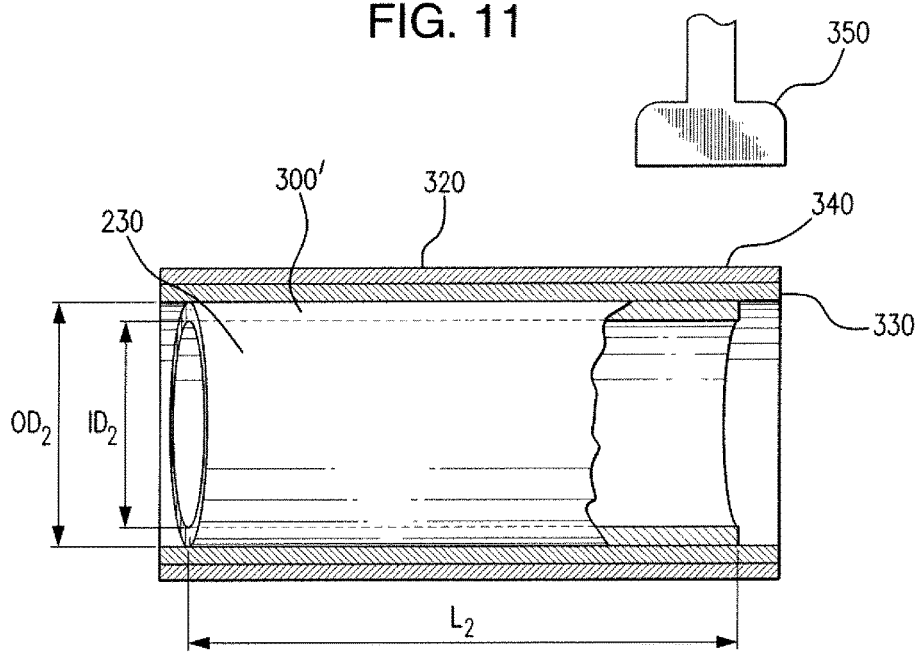
FIG. 12 illustrates the extruded tube of FIG. 11 after being radially and longitudinally expanded in the capture member.

For purpose of illustration and not limitation, FIGS. 11 and 12 depict methods of making a biaxially oriented tubular member such as the distal outer member 230 of the catheter 100 of FIG. 1 in accordance with alternative embodiments of the disclosed subject matter. For example, the method can include melt-extruding a thermoplastic polymeric material, such as in some embodiments having a relatively low Shore durometer hardness, to form a tube 300 having a lumen 310, a first inner and outer diameter ($ID_1$, $OD_1$) and a first length ($L_1$), and cooling the extruded tube 300 to a temperature (e.g., to room temperature) which is less than an elevated temperature of the melt-extrusion. The cooled extruded tube 300 is placed within a capture member 320, heated to an elevated temperature, and radially and axially expanded in the capture member 320 to a second inner and outer diameter ($ID_2$, $OD_2$) and length ($L_2$), to thereby biaxially orient the polymeric material of the extruded tube 300. FIG. 11 illustrates the extruded tube 300 disposed within the capture member 320 prior to being expanded therein, and FIG. 12 illustrates the expanded tube 300' within the capture member 320 (i.e., the extruded tube 300 of FIG. 11 after being radially and longitudinally expanded within the capture member 320). After being radially and longitudinally expanded, the resulting expanded tube 300' is cooled to room temperature and heat stabilized as discussed in more detail below.

In alternative embodiments of the disclosed subject matter and in accordance with FIG. 11, the capture member 320 can be tubular with an inner surface layer 330 of a lubricious polymeric material such as polytetrafluoroethylene (PTFE) for subsequent ease of part removal, reinforced with an outer high strength jacket layer 340 such as stainless steel tubing configured to prevent or inhibit diameter creep (growth) after repeated use. Thus, the capture member 320 can be configured to radially restrain the growing tube 300, without the inner or outer diameter of the capture member 320 increasing at the elevated internal pressures used to radially expand the extruded tube 300.

In alternative embodiments of the disclosed subject matter, the extruded tube 300 can be heated to the elevated temperature within the capture member 320, which in the illustrated embodiment comprises directing heat from a heating nozzle 350 at the outer surface of the capture member 320. In some embodiments, the heating nozzle 350 traverses along a length of the extruded tube 300, from a first end to the opposite end. Thus, the radial and longitudinal expansion can be initiated with only the first end of the extruded tube 300 heated by the nozzle 350 in some embodiments. In some embodiments, the extruded tube 300 is heated to an expansion elevated temperature which is less than the melt-extrusion elevated temperature (i.e., less than a melting temperature of the polymeric material).

In alternative embodiments of the disclosed subject matter, the extruded tube 300 can be axially expanded with a load applied on at least one end of the tube, e.g., using a vertical necking apparatus (not illustrated), and can be radially expanded with pressurized media introduced into the extruded tube lumen from a pressurized media source (not illustrated) connected to one end of the extruded tube 300. For example, with the heating nozzle 350 heating the first end of the extruded tube 300, the heating nozzle 350 can be moved toward the second end and the load is applied to the second end in the same direction as the heating nozzle movement to axially expand (i.e., stretch lengthwise) the extruded tube 300. The amount of the load required to provide the desired stretch percent depends on factors such as the tensile elongation, dimensions, material of the tubing 300, pressure of the pressurized media, and the expanded inner diameter. The pressurized media, e.g., compressed air, can be at an elevated pressure sufficient to initiate the radial expansion, such that the wall hoop stress exceeds the material resistance (typically the yield stress) to stretching at the blowing temperature. The internal pressure used to radially expand the tubing 300 can be about 400 to about 600 psi.

In alternative embodiments of the disclosed subject matter, the extruded tube 300 can be simultaneously radially and axially expanded and further necked at the elevated temperature, for ease of manufacture. Alternatively, the extruded tube 300 can be sequentially expanded (i.e., first radially then longitudinally, or first longitudinally and then radially).

In alternative embodiments of the disclosed subject matter, the tubing 300 can be radially expanded into contact with the inner surface of the capture member 310, to the second outer diameter which is about equal to the inner diameter of the capture member 310. The tubing 300 can radially expand in all directions around the tubing circumference, resulting in circumferential orientation of the polymeric material. In some embodiments, the second inner diameter ($ID_2$) can be at least about 5 times larger than the first inner diameter ($ID_1$) of the extruded tube (i.e., the blow-up-ratio, BUR, of the expanded tubular member 300' is at least about 5, and is more specifically about 5.8 to about 6). The large BUR can provide a high degree of circumferential orientation, for a large increase in the rupture pressure of the tubing. In some embodiments, the tubing can radially expanded to substantially the maximum amount possible (i.e., to a BUR which is at least about 80% of the maximum BUR possible).

As embodied herein, after biaxial expansion or necking as described above, the catheter can be subsequently assembled, at least by sealingly securing a balloon 140 to a distal end of the distal outer member 230 via heat bonding, as described herein, such that the balloon 140 has an interior in fluid communication with the inflation lumen 202 of the distal outer member 230. Portions of the catheter can be coated as known in the art, for example with a hydrophilic coating of poly(ethylene oxide) (PEO).

Catheters in accordance with the disclosed subject matter can be of any suitable dimensions, but preferably the shaft can have a reduced profile. For example, the proximal portion of the shaft can have a maximum diameter of about 0.028 inches, the midshaft can have a diameter of about 0.035 inches to about 0.038 inches, and the distal outer member can have a diameter of about 0.032 inches to about 0.034 inches. The average width at the proximal port can be about 0.033 inches. The crossing profile can be about 0.0425 inches (for a 3.0×18 mm balloon) and the tip entry profile can be about 0.017 inches. The working length of the catheter can be about 145 cm.

EXAMPLES

A 3.0 mm diameter balloon catheter was made in accordance with the disclosed subject matter and compared to known 3.0 mm diameter balloon catheters.

Example 1

The flexibility of the distal section of the balloon catheter in accordance with the disclosed subject matter was tested and compared to known balloon catheters including the Synergy II® (commercially available from Boston Scientific), Promus Premier® (commercially available from Boston Scientific), and Resolute Integrity® (commercially available from Medtronic). For example, a tip flick test was performed, which "flicks" the tip of the catheter by applying a load to the tip and measuring how much the tip deflects due to this applied load, measuring its stiffness. The stiffness of the tip is plotted versus the distance from the distal end of the tip. A higher slope values indicate a higher bending stiffness.

Figure 15:
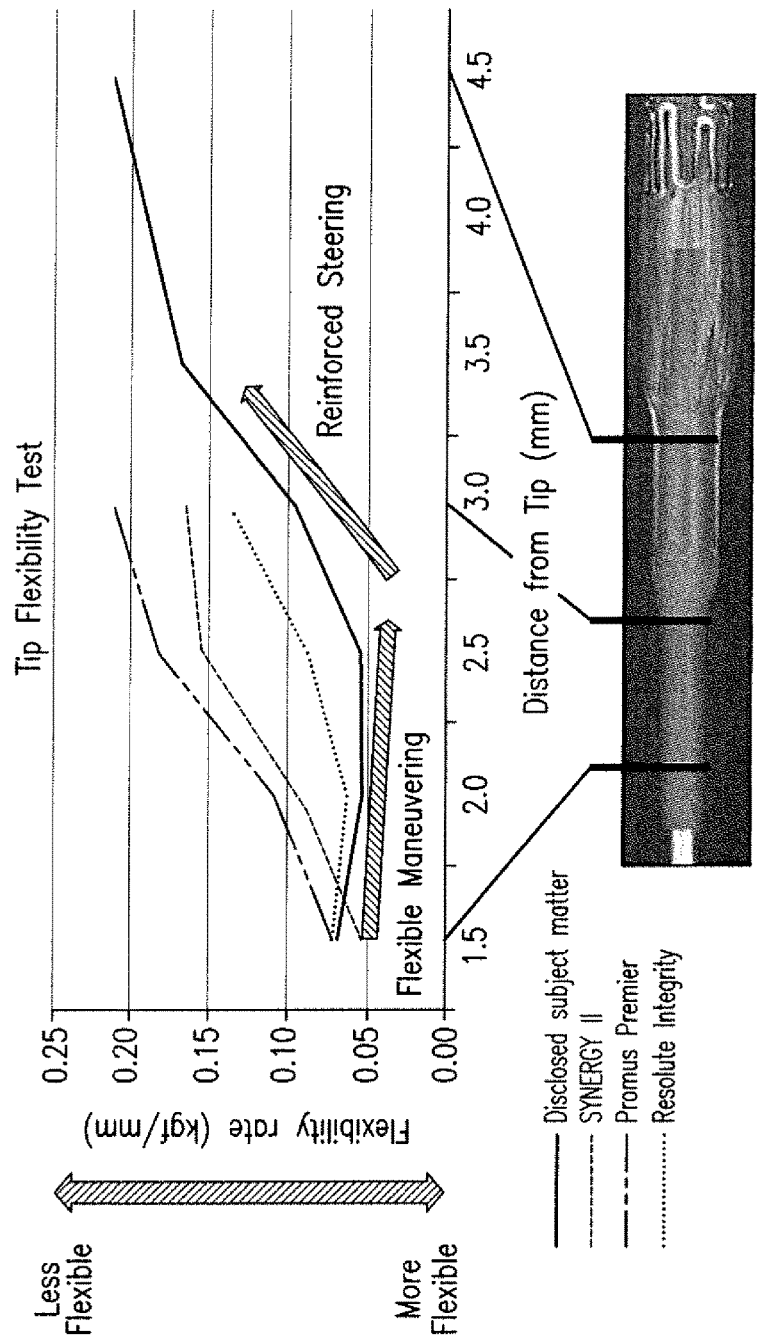
FIG. 15 is plot of the flexibility of the distal section of an exemplary balloon catheter in accordance with the disclosed subject as compared to commercially available catheters.

The results of the testing are shown in FIG. 15, which plots the flexibility rate (in kgf/mm) against the distance from the distal end of the catheter (in mm). As depicted, catheters in accordance with the disclosed subject matter unexpectedly provide an improved combination of flexibility and support as compared to commercially available balloon catheters. As shown in FIG. 15, the portion of the catheter between about 1.5 mm to about 3 mm from the distal end of the catheter (i.e., the tip) in accordance with the disclosed subject matter has improved flexibility (i.e., a lower flexibility rate) as compared to known commercially available catheters, which provides improved maneuverability within the vessel of a patient. Yet the portion of the catheter between about 3 mm and about 4.5 mm (i.e., along the length of the distal seal portion) has a higher flexibility rate (i.e., is less flexible) than the more distal section, which can provide for reinforced support to steer through the vessel of a patient.

Example 2

Figure 16:
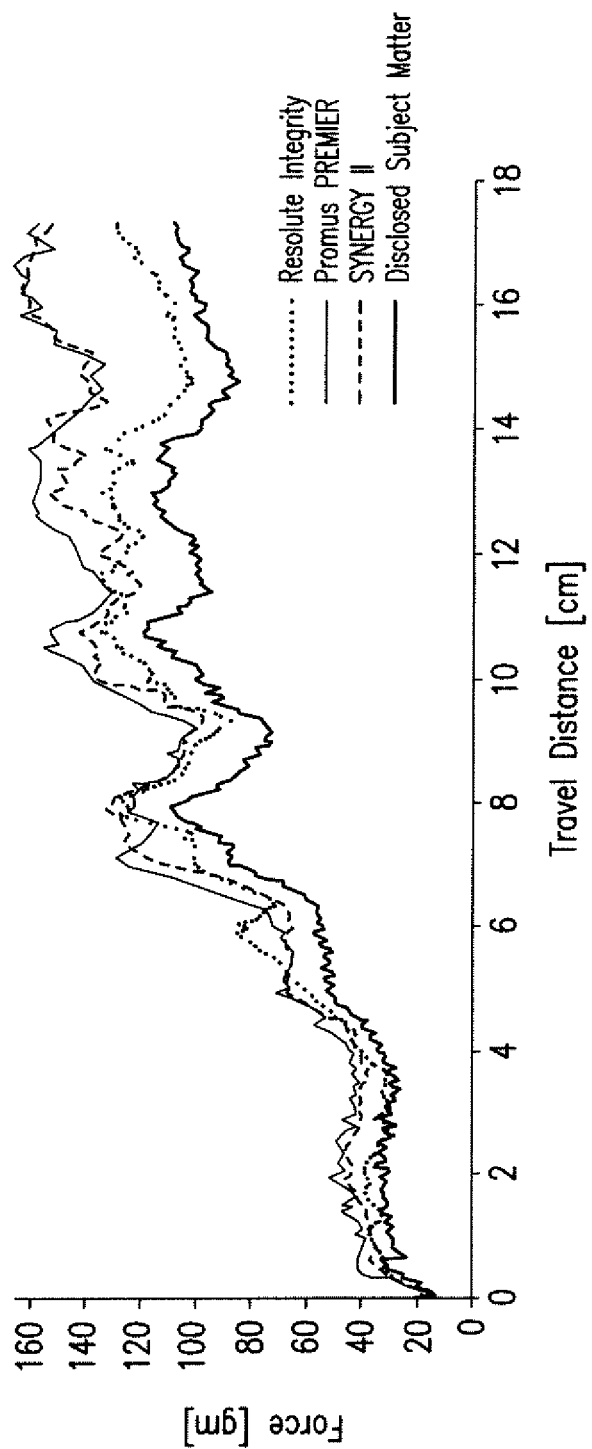
FIG. 16 is plot of the force required to track a catheter along a travel distance for an exemplary balloon catheter in accordance with the disclosed subject as compared to commercially available catheters.

The trackability of the balloon catheter in accordance with the disclosed subject matter prepared as described above was tested and compared to known balloon catheters including the Synergy II® (commercially available from Boston Scientific), Promus Premier® (commercially available from Boston Scientific), and Resolute Integrity® (commercially available from Medtronic). Trackability was tested by measuring the proximal force required to advance a catheter through a tortuosity fixture (simulating a tortuous anatomy) over a guide wire. Lower forces indicate a more flexible and deliverable catheter. The results of the testing are shown in FIG. 16, which shows the force required to track the catheter along the travel distance. A lower force represents a more trackable catheter. As depicted, catheters in accordance with the disclosed subject matter having a zero transmission (i.e., monolithic) inner member bonded to a distal balloon shafting having a portion free of attachment and a distal outer member necked along its entire length and made of PEBAX® 72 D unexpectedly provide improved trackability compared to commercially available catheters. For example, the catheter in accordance with the disclosed subject matter requires up to 30% less work than commercially available catheters, which can improve delivery and navigation through a tortuous vessel, including by reducing the time to reach the target site.

Example 3

Figure 17:
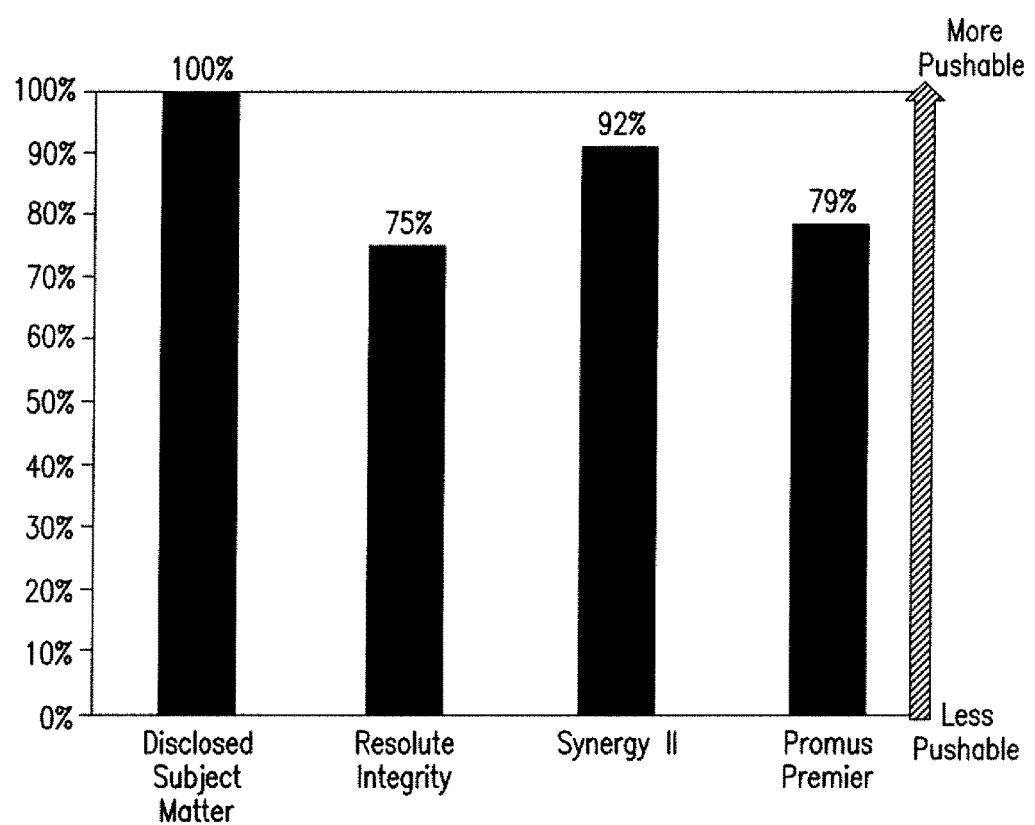
FIG. 17 is comparison of the pushability of an exemplary balloon catheter in accordance with the disclosed subject as compared to commercially available catheters.

The pushability of the balloon catheter in accordance with the disclosed subject matter prepared as described above was tested and compared to known balloon catheters including the Synergy II® (commercially available from Boston Scientific), Promus Premier® (commercially available from Boston Scientific), and Resolute Integrity® (commercially available from Medtronic). Pushability (i.e., push efficiency) was tested by applying a known force to the proximal end of a catheter placed in a tortuosity fixture over a guide wire (simulating a tortuous anatomy) and measuring how much of this force is transmitted to the distal end of the catheter. Higher ratios of distal force over proximal force indicate higher pushability. The results of the testing are shown in FIG. 17, which shows the pushability of the catheter. As depicted, catheters in accordance with the disclosed subject matter having a hypotube with a stepped skive in combination with a zero transmission (i.e., monolithic) inner member unexpectedly provide improved pushability as compared to commercially available catheters. For example, the catheter in accordance with the disclosed subject matter provided up to 33% improved pushability than commercially available catheters, which can improve delivery of the catheter to, including time needed to reach, the target site in a patient.

Example 4

Figure 18:
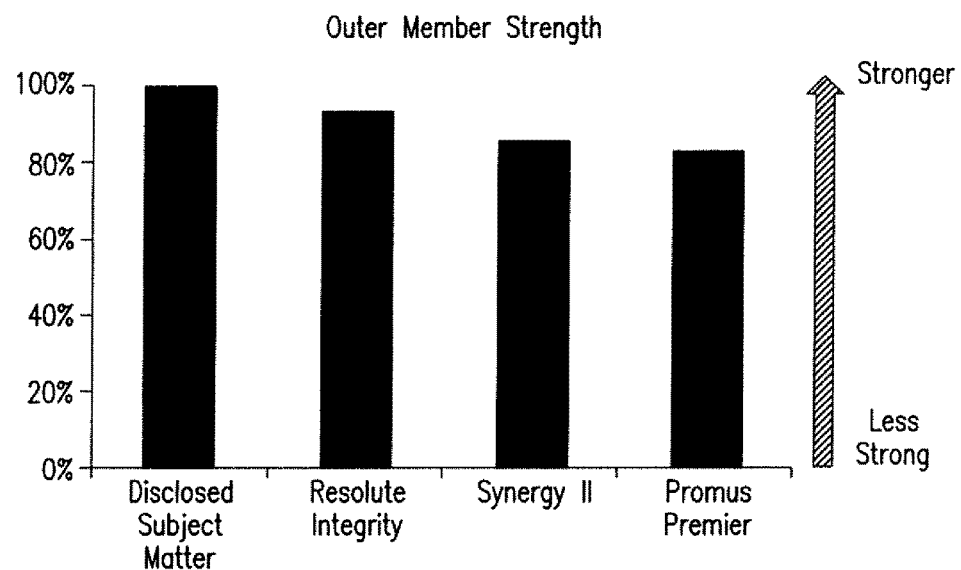
FIG. 18 is comparison of the tensile strength of the distal outer member of an exemplary balloon catheter in accordance with the disclosed subject as compared to commercially available catheters.

The strength of distal outer member in accordance with the disclosed subject matter prepared as described above was tested and compared to known balloon catheters including the Synergy II® (commercially available from Boston Scientific), Promus Premier® (commercially available from Boston Scientific), and Resolute Integrity® (commercially available from Medtronic). Distal outer member strength was tested by applying a tensile force to determine the strength of the distal section of a device. Higher force values indicate a higher distal tensile strength. The results of the testing are shown in FIG. 18, which shows that catheters in accordance with the disclosed subject matter having a single layer necked PEBAX® 72 D outer member unexpectedly provide improved strength as compared to commercially available catheters. For example, the catheter in accordance with the disclosed subject matter was up 21% stronger than commercially available catheters, which can provide improved strength in navigating complex anatomy and reduce the likelihood of rupture/failure.

Example 5

Figure 19:
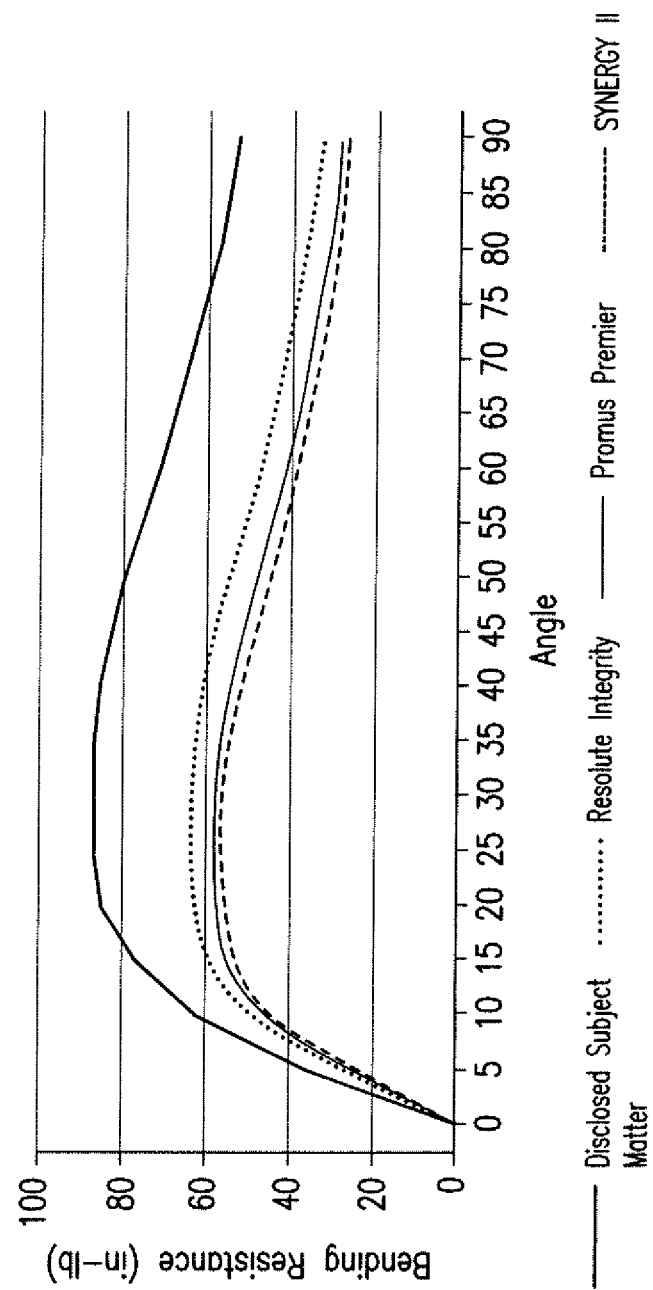
FIG. 19 is plot of the bending resistance against the angle for a hypotube of an exemplary balloon catheter in accordance with the disclosed subject as compared to commercially available catheters.

The strength of the hypotube of the balloon catheter in accordance with the disclosed subject matter prepared as described above was tested and compared to known balloon catheters including the Synergy II® (commercially available from Boston Scientific), Promus Premier® (commercially available from Boston Scientific), and Resolute Integrity® (commercially available from Medtronic). The strength of the hypotube was tested by applying a bending force perpendicular to the main axis of a straight portion of the hypotube until it is bent by 90°. The higher the force it takes to bend the hypotube a certain angle (bending modulus), the higher its bending resistance and thus its strength. The results of the testing are shown in FIG. 19, which plots the bending resistance (in-lb) against the angle. A higher bending resistance represents a stronger hypotube. As depicted in FIG. 19, catheters in accordance with the disclosed subject matter having a hypotube with the dimensions and the stepped skive provided herein unexpectedly provide improved strength as compared to commercially available catheters. For example, the catheter in accordance with the disclosed subject matter was up 60% stronger than commercially available catheters, which can provide improved push transmission, a reduction in the tendency to kink, and smoother force transfer and tactile feedback.

Example 6

Figure 20A:
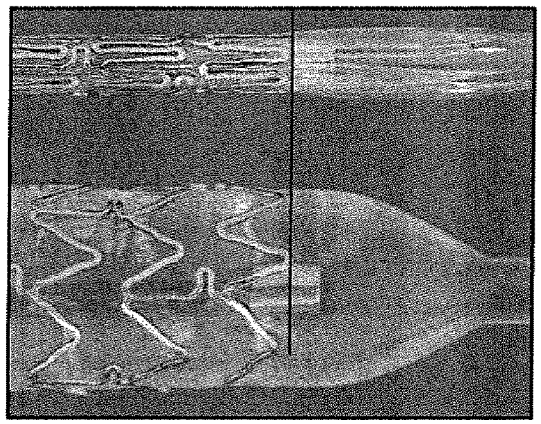
FIG. 20A is a photo of a stent mounted on a balloon of an exemplary balloon catheter in accordance with the disclosed subject.
Figure 20B:
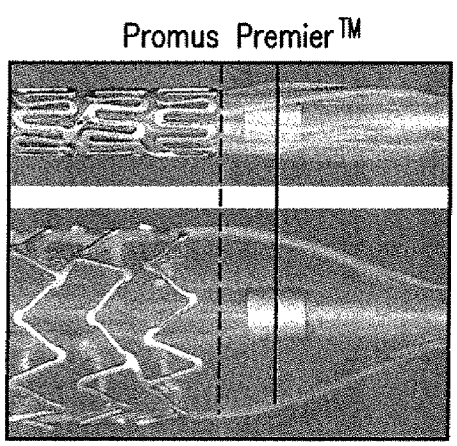
FIGS. 20B and 20C are photos of stents mounted on balloons of commercially available balloon catheters.
Figure 20C:
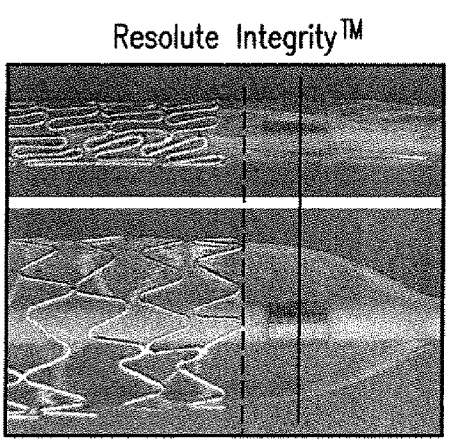

The marker placement of the balloon catheter in accordance with the disclosed subject matter prepared as described above was measured and compared to known balloon catheters including the Promus Premier® (commercially available from Boston Scientific), and Resolute Integrity® (commercially available from Medtronic). The results of the measurement are shown in Table 1 below. As shown in the table, catheters in accordance with the disclosed subject matter have improved marker placement precision as compared to commercially available catheters. For example, the catheter in accordance with the disclosed subject matter provided less than 0.1 mm in distance between the end of the stent and midpoint of the marker, which can provide improved stent deployment at the precise location of a lesion as compared to commercially available catheters which had between about 0.9 mm to 1.7 mm in distance between the end of the stent and midpoint of the marker. FIGS. 20A, 20B, and 20C further demonstrate the improved stent placement for the disclosed subject matter (FIG. 20A) as compared to the Promus Premier® (FIG. 20B) and Resolute Integrity® (FIG. 20C).

TABLE 1

| Product | Distance between proximal stent end and mid marker average (mm) | Distance between distal stent end and mid marker average (mm) |
| --- | --- | --- |
| 3.0 × 18 mm balloon catheter in accordance with disclosed subject matter | 0.1 | 0.00 |
| 3.0 × 18 mm Resolute Integrity ® | 1.4 | 1.7 |
| 3.0 × 20 mm Promus Premier ® | 0.9 | 0.9 |

Example 7

Figure 21:
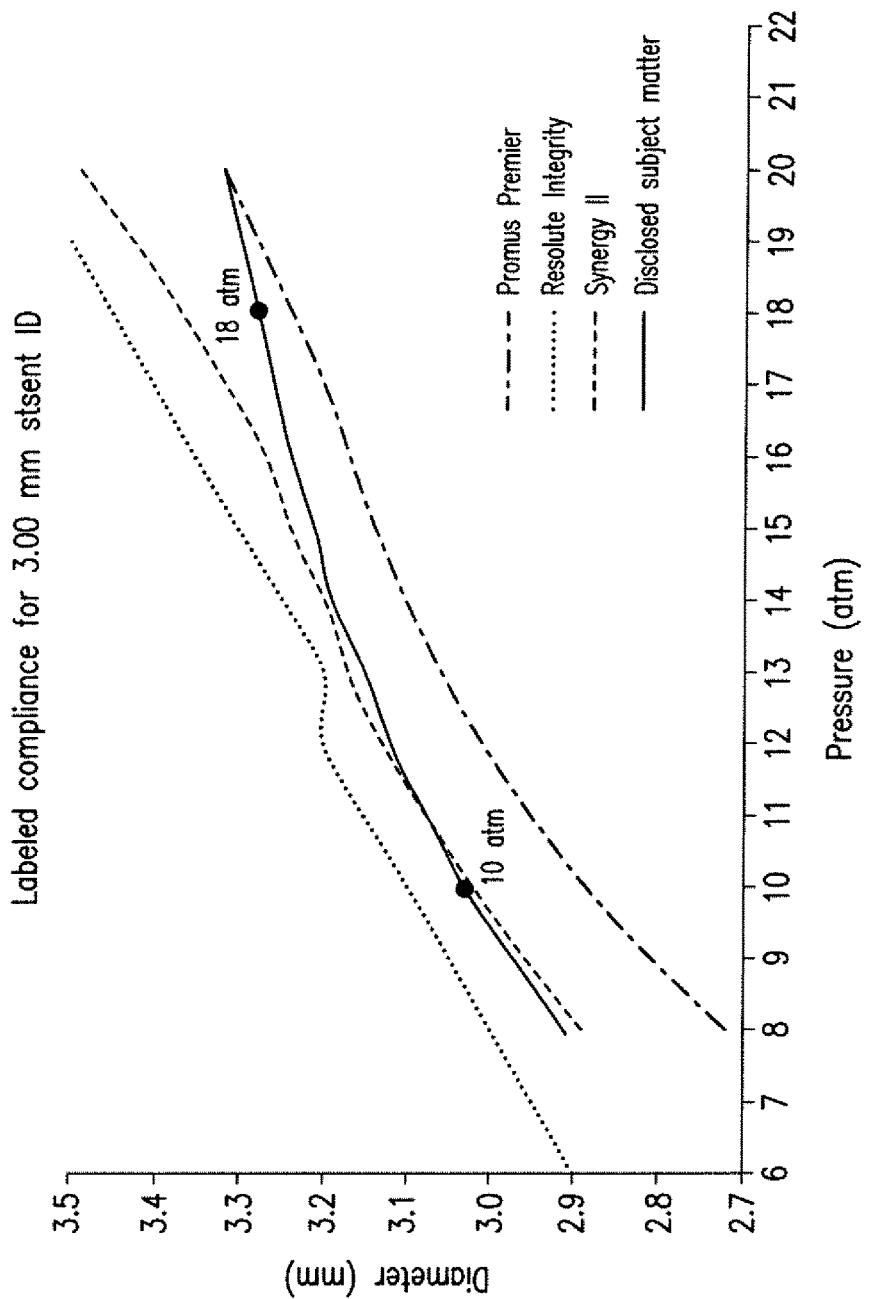
FIG. 21 is plot of the diameter of the balloon as a function of pressure for an exemplary balloon catheter in accordance with the disclosed subject as compared to commercially available catheters.

The compliance of the balloon of the catheter in accordance with the disclosed subject matter prepared as described above was tested and compared to known balloon catheters including the Synergy II® (commercially available from Boston Scientific), Promus Premier® (commercially available from Boston Scientific), and Resolute Integrity® (commercially available from Medtronic). The results of the testing are shown in FIG. 21, which is a plot of the diameter of the balloon as a function of pressure. As depicted, balloons in accordance with the disclosed subject matter having an inner layer of PEBAX® 63 D and an outer layer of PEBAX® 72 D unexpectedly provide a flatter compliance as compared to commercially available catheters, which can provide more controlled growth in expansion during delivery and enable higher pressure deployment for improved stent expansion apposition with a decreased risk of over-expansion of the vessel as compared to commercially available catheters. A flatter compliance can provide focalized application of force in a lesion without concern of over-expansion in vessel areas outside of the lesion (i.e., "focalized force application"). Additional compliance data for balloons in accordance with the disclosed subject matter is provided in Table 2 below.

TABLE 2

| Pressure (atm) | 2.0 mm | 2.25 mm | 2.5 mm | 2.75 mm | 3.0 mm | 3.25 mm | 3.5 mm | 4.0 mm |
| --- | --- | --- | --- | --- | --- | --- | --- | --- |
| 8 | 1.87 | 2.14 | 2.41 | 2.71 | 2.91 | 3.10 | 3.37 | 3.85 |
| 9 | 1.91 | 2.19 | 2.46 | 2.77 | 2.97 | 3.16 | 3.43 | 3.92 |
| 10 (Nominal) | 1.96 | 2.23 | 2.51 | 2.81 | 3.03 | 3.22 | 3.49 | 3.99 |
| 11 | 1.99 | 2.27 | 2.55 | 2.87 | 3.08 | 3.28 | 3.55 | 4.05 |
| 12 | 2.02 | 2.30 | 2.59 | 2.90 | 3.12 | 3.33 | 3.60 | 4.11 |
| 13 | 2.05 | 2.34 | 2.62 | 2.94 | 3.15 | 3.37 | 3.65 | 4.15 |
| 14 | 2.08 | 2.37 | 2.66 | 2.97 | 3.19 | 3.41 | 3.69 | 4.20 |
| 15 | 2.11 | 2.39 | 2.68 | 3.00 | 3.21 | 3.44 | 3.72 | 4.24 |
| 16 | 2.13 | 2.42 | 2.71 | 3.02 | 3.24 | 3.47 | 3.75 | 4.27 |
| 17 | 2.14 | 2.44 | 2.73 | 3.04 | 3.26 | 3.50 | 3.78 | 4.30 |
| 18 (RBP) | 2.16 | 2.46 | 2.74 | 3.07 | 3.28 | 3.52 | 3.81 | 4.33 |
| 19 | 2.18 | 2.48 | 2.76 | 3.09 | 3.30 | 3.54 | 3.83 | 4.35 |
| 20 | 2.19 | 2.49 | 2.77 | 3.11 | 3.32 | 3.56 | 3.85 | 4.38 |

Example 8

The distal catheter tensile strength of the balloon catheter in accordance with the disclosed subject matter prepared as described above was measured and compared to commercially available catheters. The results of the measurement are shown in Table 3 below. As shown in the table, catheters in accordance with the disclosed subject matter have tensile strengths that exceed the ISO10555-1:2013 standard that specifies a minimum peak tensile of 5 N for test pieces that range from 0.75 mm to not more than 1.15 mm. For example, the average distal catheter tensile strength for all sizes was 17 N, which was 5 N higher than other commercially available catheters.

TABLE 3

| | Disclosed Subject Matter | Commercially Available Catheters |
| --- | --- | --- |
| Number tests | 371 | 1056 |
| Avg. Tensile Strength (N) | 17 | 12 |

The distal catheter tensile strength at the proximal balloon shaft seal for small size balloon catheters in accordance with the disclosed subject matter was also measured. The results of the measurement are shown in Table 4 below. As shown in the table, catheters in accordance with the disclosed subject matter provided sufficient tensile strengths that exceed the ISO10555-1:2013 standard that specifies a minimum peak tensile of 5 N for test pieces that range from 0.75 mm to not more than 1.15 mm.

TABLE 4

|  | 2.0 mm | 2.25 mm | 2.5 mm |
| --- | --- | --- | --- |
| Number tests | 61 | 13 | 15 |
| Avg. Tensile Strength (N) | 10 | 15 | 16 |

Although illustrated as a rapid exchange type balloon dilatation catheter, it should be understood that the disclosed subject matter can be used in a variety of catheters and catheter configurations, including stent delivery balloon catheters and non-rapid exchange type catheters. For example, in some embodiments an over-the-wire type catheter is provided having a full length inner tubular member with a guidewire lumen which extends from the proximal to the distal end of the catheter. The over-the-wire catheter can include any of the features described herein above except the proximal port. For example, the over-the-wire catheter can include the distal balloon shaft, tip, and inner member design and/or the distal outer member design described herein above.

While the present disclosed subject matter is described herein in terms of certain embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A catheter comprising:
an outer shaft member having a proximal section and a distal outer member, the outer shaft having an inflation lumen defined therethrough;
a balloon in fluid communication with the inflation lumen, the balloon having a proximal balloon shaft, a proximal cone portion, a working length, a distal cone portion, and a distal balloon shaft, wherein the proximal balloon shaft is coupled to the distal outer member; and
a monolithic inner tubular member having guidewire lumen defined therethrough, the monolithic inner tubular member extending from the outer shaft proximal section through the distal outer member and through the balloon to form a tip,
wherein the distal balloon shaft has an inner diameter and comprises a distal seal portion coupled to the inner tubular member and a proximal portion free of attachment to the inner tubular member and monolithic with the distal seal portion, and wherein the inner diameter is constant across the proximal portion of the distal balloon shaft and the distal seal portion, and the length of the proximal portion of the distal balloon shaft is at least two times the inner diameter of the distal balloon shaft.

2. The catheter according to claim 1, wherein the tip includes a distal exposed portion distal of the distal seal portion of the distal balloon shaft and a proximal portion along the length of the distal seal portion of the distal balloon shaft.

3. The catheter according to claim 2, wherein the length of the proximal portion of the distal balloon shaft is 35% to 70% the length of the tip.

4. The catheter according to claim 2, wherein the length of the proximal portion of the distal balloon shaft is 50% to 120% the length of the distal exposed portion of the tip.

5. The catheter according to claim 2, wherein the length of the proximal portion of the distal balloon shaft is 25% to 40% of the combined length of the distal balloon shaft and the distal exposed portion of the tip.

6. The catheter according to claim 1, wherein the inner diameter of the distal balloon shaft is 0.68 mm to 0.87 mm.

7. The catheter according to claim 1, wherein the length of the proximal portion of the distal balloon shaft is at least 1.4 mm.

8. The catheter according to claim 7, wherein the length of the proximal portion of the distal balloon shaft is 1.9 mm.

9. The catheter according to claim 1, wherein the length of the distal seal portion of the distal balloon shaft is 1.4 mm.

10. The catheter according to claim 2, wherein the length of the tip is 3.0 mm to 5.0 mm.

11. The catheter according to claim 2, wherein the length of the distal exposed portion of tip is 1.6 mm to 3.6 mm.

12. The catheter according to claim 1, wherein the distal outer member comprises a single layer of polyether block amide.

13. The catheter according to claim 12, wherein the distal outer member is necked to a reduced diameter along an entire length of the distal outer member.

14. The catheter according to claim 13, wherein the reduced diameter comprises an outer diameter of 0.032 inches to 0.034 inches.

15. The catheter according to claim 13, wherein the reduced diameter comprises an inner diameter of 0.031 inches.

16. The catheter according to claim 1, wherein the proximal section of the outer shaft comprises a hypotube having a proximal section and a distal section with the inflation lumen and a longitudinal axis defined therethrough, the distal section having a skive defined by a first angled cut, an axial cut, and a second angled cut.

17. The catheter according to claim 16, wherein the first angled cut has a length of 25 mm, the axial cut has a length of 25 mm, and the second angled cut has a length of 100 mm.

18. The catheter according to claim 16, wherein the axial cut has a height of 0.0065 inches to 0.0075 inches.

19. The catheter according to claim 16, wherein the second angled cut defines a distal edge height of 0.0035 inches to 0.0045 inches.

20. The catheter according to claim 16, wherein the proximal section of the hypotube has an outer diameter of 0.0275 inches to 0.0285 inches and an inner diameter of 0.0195 inches to 0.0205 inches.

21. The catheter according to claim 16, wherein the proximal section of the outer shaft further comprises a midshaft member including the guidewire lumen and the inflation lumen defined therethrough, the inflation lumen along the midshaft member being configured to receive at least a portion of the distal section of the hypotube.

22. A method of making a catheter, comprising:
providing an outer shaft member having a proximal section and a distal outer member, the outer shaft having an inflation lumen defined therethrough;
providing a balloon in fluid communication with the inflation lumen, the balloon having a proximal balloon shaft, a proximal cone portion, a working length, a distal cone portion, and a distal balloon shaft having an inner diameter;
coupling the proximal balloon shaft to the distal outer member;
providing a monolithic inner tubular member having guidewire lumen defined therethrough, the monolithic inner tubular member extending from the outer shaft proximal section through the distal outer member and through the balloon to form a tip; and
and coupling a distal seal portion of the distal balloon shaft to the inner tubular member, wherein the distal balloon shaft includes a proximal portion free of attachment to the inner tubular member and monolithic with the distal seal portion, and wherein the inner diameter is constant across the proximal portion of the distal balloon shaft and the distal seal portion, and further wherein the length of the proximal portion of the distal balloon shaft is at least two times the inner diameter of the distal balloon shaft.

23. The method according to claim 22, further comprising necking the distal outer member from a first outer diameter of 0.041 inches to a reduced outer diameter of 0.032 inches to 0.034 inches along an entire length of the distal outer member.

24. The method according to claim 23, wherein the distal outer member has a first inner diameter of 0.033 inches before necking and a reduced inner diameter of 0.031 inches along an entire length of the distal outer member after necking.

25. A catheter comprising:
an outer shaft member having a proximal section and a distal outer member, the outer shaft having an inflation lumen defined therethrough, the distal outer member comprising a single layer of polyether block amide necked to a reduced diameter along an entire length of the distal outer member;
a balloon in fluid communication with the inflation lumen, the balloon having a proximal balloon shaft, a proximal cone portion, a working length, a distal cone portion, and a distal balloon shaft, wherein the proximal balloon shaft is coupled to the distal outer member; and
a monolithic inner tubular member having guidewire lumen defined therethrough, the monolithic inner tubular member extending from the outer shaft proximal section through the distal outer member and through the balloon to form a tip,
wherein the distal balloon shaft has an inner diameter and comprises a distal seal portion coupled to the inner tubular member and a proximal portion free of attachment to the inner tubular member and monolithic with the distal seal portion, and wherein the inner diameter is constant across the proximal portion of the distal balloon shaft and the distal seal portion, and the length of the proximal portion of the distal balloon shaft is at least two times the inner diameter of the distal balloon shaft, and wherein the proximal section of the outer shaft comprises a hypotube having a proximal section and a distal section with the inflation lumen and a longitudinal axis defined therethrough, the distal section having a skive defined by a first angled cut, an axial cut, and a second angled cut.

* * * * *